(12) United States Patent
Wada

(10) Patent No.: US 12,201,962 B2
(45) Date of Patent: Jan. 21, 2025

(54) METHOD FOR PRODUCING PARTICULATE WATER ABSORBENT, AND PARTICULATE WATER ABSORBENT

(71) Applicant: NIPPON SHOKUBAI CO., LTD., Osaka (JP)

(72) Inventor: Takaaki Wada, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 900 days.

(21) Appl. No.: 17/289,495

(22) PCT Filed: Nov. 7, 2019

(86) PCT No.: PCT/JP2019/043707
§ 371 (c)(1),
(2) Date: Apr. 28, 2021

(87) PCT Pub. No.: WO2020/096003
PCT Pub. Date: May 14, 2020

(65) Prior Publication Data
US 2021/0387163 A1 Dec. 16, 2021

(30) Foreign Application Priority Data

Nov. 7, 2018 (JP) ................................ 2018-209791

(51) Int. Cl.
*B01J 20/28* (2006.01)
*B01J 20/26* (2006.01)
(Continued)

(52) U.S. Cl.
CPC ....... *B01J 20/267* (2013.01); *B01J 20/28004* (2013.01); *B01J 20/28016* (2013.01); *B01J 20/3085* (2013.01); *C08J 3/245* (2013.01)

(58) Field of Classification Search
None
See application file for complete search history.

(56) References Cited

U.S. PATENT DOCUMENTS 7,510,988 B2 * 3/2009 Wada ................ C08J 3/24
428/206
8,596,931 B2 * 12/2013 Nagashima ............ B01J 20/267
406/197
(Continued)

FOREIGN PATENT DOCUMENTS

CN 103459473 A 12/2013
CN 107383728 A 11/2017
(Continued)

OTHER PUBLICATIONS

International Preliminary Report on Patentability from corresponding PCT Application No. PCT/JP2019/043707 dated May 11, 2021.
(Continued)

*Primary Examiner* — Joseph D Anthony
(74) *Attorney, Agent, or Firm* — Harness Dickey & Pierce P.L.C.

(57) ABSTRACT

Provided is a method for producing a particulate water-absorbing agent that can reduce a re-wet amount of an absorbent body when applied to the absorbent body. The method for producing the particulate water-absorbing agent according to an aspect of the present invention includes the step of surface-crosslinking a water-absorbing resin powder with use of a surface-crosslinking agent, wherein the water-absorbing resin powder has a specific surface area index, expressed by formula (1) below, of not less than 1.5, and the surface-crosslinking agent has an apparent Hansen solubility parameter of 22.5 $MPa^{1/2}$ to 28.5 $MPa^{1/2}$:

(specific surface area index)=(specific surface area of water-absorbing resin powder)/($10^8 \times D50^2$)   (1), (Continued)

where:
in formula (1), the unit of the specific surface area index is [1/kg], the unit of the specific surface area is [m²/kg], D50 denotes a mass average particle diameter, and the unit of D50 is [m].

10 Claims, 1 Drawing Sheet

(51) Int. Cl.
*B01J 20/30* (2006.01)
*C08J 3/24* (2006.01)

(56) References Cited

U.S. PATENT DOCUMENTS

| | | |
|---|---|---|
| 2014/0031473 A1 | 1/2014 | Nogi et al. |
| 2014/0042364 A1 | 2/2014 | Nogi et al. |
| 2014/0312273 A1 | 10/2014 | Wattebled et al. |
| 2015/0315321 A1 | 11/2015 | Won et al. |
| 2018/0244867 A1 | 8/2018 | Kim et al. |

FOREIGN PATENT DOCUMENTS

| | | |
|---|---|---|
| EP | 2669318 A1 | 12/2013 |
| EP | 2669319 A1 | 12/2013 |
| JP | H4106108 A | 4/1992 |
| JP | 2002284751 A | 10/2002 |
| JP | 2014533312 A | 12/2014 |
| JP | 2016516877 A | 6/2016 |
| WO | 2012102406 A1 | 8/2012 |
| WO | 2017111205 A1 | 6/2017 |

OTHER PUBLICATIONS

International Search Report from corresponding PCT Application No. PCT/JP2019/043707 dated Feb. 10, 2020.
Extended European Search Report from corresponding European Patent Application No. 19882824.6.

\* cited by examiner

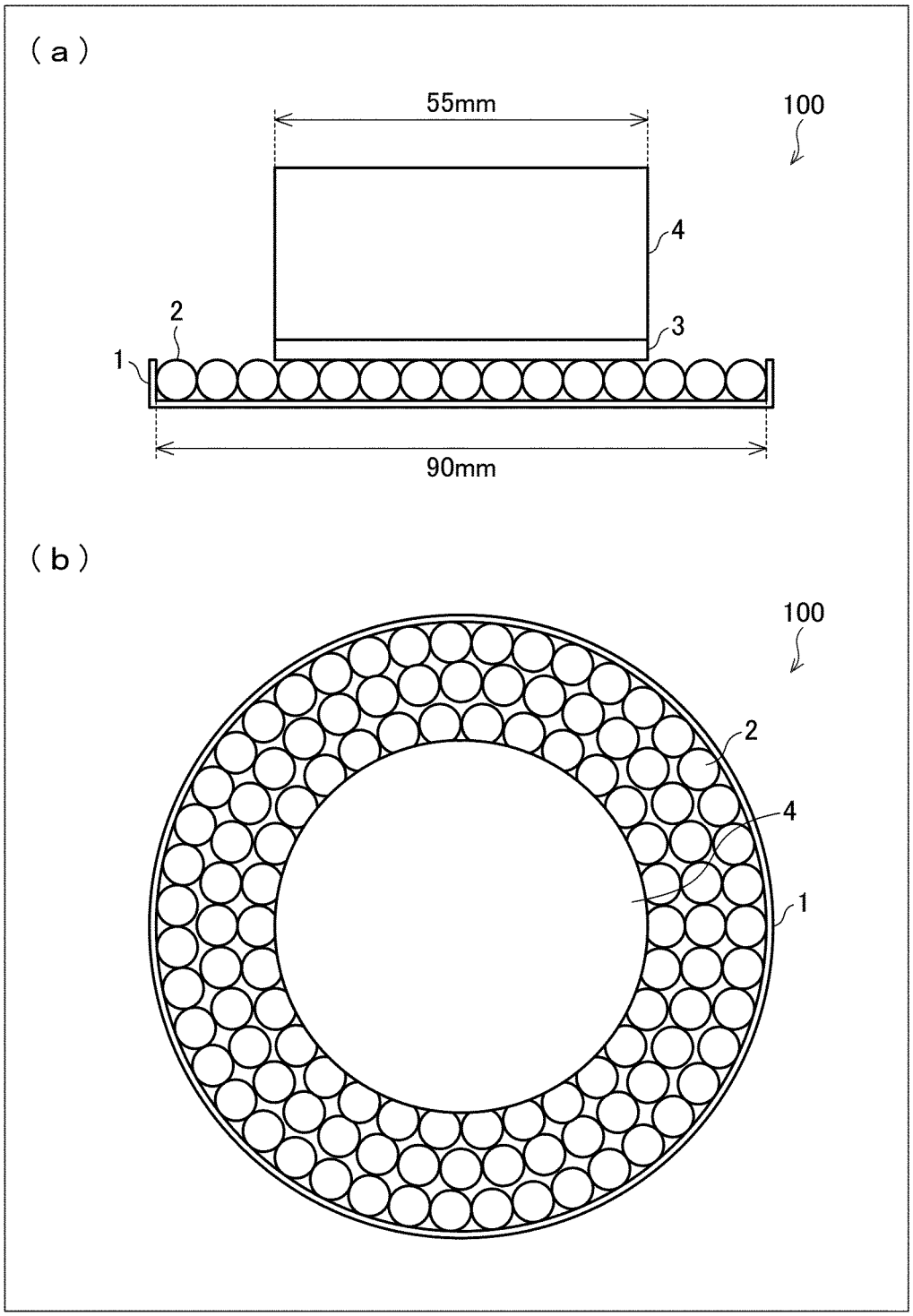

METHOD FOR PRODUCING PARTICULATE WATER ABSORBENT, AND PARTICULATE WATER ABSORBENT

PRIORITY STATEMENT

This application is a national stage application under 35 U.S.C. § 371 of PCT International Application No. PCT/JP2019/043707, which has an international filing date of 7 Nov. 2019 and claims priority under 35 U.S.C. § 119 to Japanese Patent Application No. 2018-209791 filed on 7 Nov. 2018. The contents of each application recited above are incorporated herein by reference in their entirety.

TECHNICAL FIELD

The present invention relates to a method for producing a particulate water absorbent (particulate water-absorbing agent production method) and a particulate water absorbent (particulate water-absorbing agent).

BACKGROUND ART

Particulate water-absorbing agents are used for various purposes, such as for an absorbent article (e.g., a paper diaper, a sanitary napkin, and an incontinence pad), an agricultural soil water retainer, and an industrial waterproofing agent. Particularly, the absorbent article has been developed into a wide variety of goods for people of wide generations from infants to adults. Along with this, the particulate water-absorbing agent is also required to improve its performance in various ways.

In order to improve the performance of the particulate water-absorbing agent, there have been developed particulate water-absorbing agent production methods involving use of surface-crosslinking agents having been devised in various ways. For example, Patent Literature 1 discloses a particulate water-absorbing agent production method that uses a surface-crosslinking agent defined by a specific solubility parameter. For another example, Patent Literature 2 discloses a particulate water-absorbing agent production method that uses neopentyl glycol as a surface-crosslinking agent.

CITATION LIST

Patent Literature

[Patent Literature 1]
Published Japanese Translation of PCT International Application Tokuhyo No. 2016-516877 (published on Jun. 9, 2016)

Patent Literature 2

Pamphlet of International Publication No. WO 2017/111205 (published on Jun. 29, 2017)

SUMMARY OF INVENTION

Technical Problem

However, in a case where the particulate water-absorbing agents according to the above-described conventional techniques are applied to an absorbent body in an absorbent article, each particulate water-absorbing agent allows a liquid once absorbed into the absorbent body to go outside a surface of the absorbent body again in a large amount (hereinafter, the amount of such a liquid will be referred to as a "re-wet amount"), disadvantageously. On this point, the particulate water-absorbing agent according to the above-described conventional techniques has a room for improvement.

An aspect of the present invention has an object to provide a method for producing a particulate water-absorbing agent that can reduce a re-wet amount of an absorbent body in a case where the particulate water-absorbing agent is applied to the absorbent body.

Solution to Problem

In order to attain the object, a method for producing a particulate water-absorbing agent in accordance with an aspect of the present invention includes the step of surface-crosslinking a water-absorbing resin powder with use of a surface-crosslinking agent, wherein the water-absorbing resin powder has a specific surface area index of not less than wr1.5, the specific surface area index being expressed by formula (1) below, and the surface-crosslinking agent has an apparent Hansen solubility parameter of 22.5 $MPa^{1/2}$ to 28.5 $MPa^{1/2}$:

$$(\text{specific surface area index}) = (\text{specific surface area of water-absorbing resin powder})/(10^8 \times D50^2) \quad (1),$$

where:
in formula (1), a unit of the specific surface area index is [1/kg], a unit of the specific surface area is [$m^2$/kg], D50 denotes a mass average particle diameter, and a unit of D50 is [m].

A method for producing a particulate water-absorbing agent in accordance with another aspect of the present invention includes the step of surface-crosslinking a water-absorbing resin powder with use of a surface-crosslinking agent, wherein the water-absorbing resin powder has a specific surface area index of not less than 1.5, the specific surface area index being expressed by formula (1) below, and the surface-crosslinking agent contains a $C_{6-8}$ polyhydric alcohol:

$$(\text{specific surface area index}) = (\text{specific surface area of water-absorbing resin powder})/(10^8 \times D50^2) \quad (1),$$

where:
in formula (1), a unit of the specific surface area index is [1/kg], a unit of the specific surface area is [$m^2$/kg], D50 denotes a mass average particle diameter, and a unit of D50 is [m].

A particulate water-absorbing agent in accordance with an aspect of the present invention has a specific surface area index of not less than 1.5, the specific surface area index being expressed by formula (1a) below,
the particulate water-absorbing agent having an alcohol absorbency parameter within a range defined by formulae (2) and (3) below:

$$(\text{specific surface area index}) = (\text{specific surface area of particulate water-absorbing agent})/(10^8 \times D50^2) \quad (1a);$$

$$CRC(35\% \text{ EtOH})/CRC \geq 1.2 \quad (2); \text{ and}$$

$$CRC(60\% \text{ PG})/CRC \geq 0.40 \quad (3),$$

where:
in formula (1a), a unit of the specific surface area index is [1/kg], a unit of the specific surface area is [$m^2$/kg], D50 denotes a mass average particle diameter, and a unit of D50 is [m];

in formula (2), CRC (35% EtOH) denotes a CRC measured with use of a 35 mass % aqueous ethanol solution; and in formula (3), CRC (60% PG) denotes a CRC measured with use of a 60 mass % aqueous 1,2-propylene glycol solution.

Advantageous Effects of Invention

In accordance with an aspect of the present invention, it is possible to provide a method for producing a particulate water-absorbing agent production that can reduce a re-wet amount of an absorbent body in a case where the particulate water-absorbing agent is applied to the absorbent body.

BRIEF DESCRIPTION OF DRAWINGS (a) and (b) of FIG. 1 show a measurement device, used in the Examples of the present application, for measuring a re-wet amount specific to a particulate water-absorbing agent itself (hereinafter, such a re-wet amount will be simply referred to as a "specific re-wet"). (a) of FIG. 1 is a side view of the measurement device, whereas (b) of FIG. 1 is a top view of the measurement device.

DESCRIPTION OF EMBODIMENTS

The following provides a specific description of a method for producing a particulate water-absorbing agent in accordance with an aspect of the present invention. However, the scope of the present invention is not restricted by the description, and encompasses modes not illustrated below and modes appropriately changed or implemented from those described below within the gist of the present invention. Specifically, the present invention is not limited to the embodiments, but can be altered by a skilled person in the art within the scope of the claims. The present invention also encompasses, in its technical scope, any embodiment derived by combining technical means disclosed in differing embodiments.

Technical Ideas of the Present Invention

Prior to descriptions of individual matters, a brief description of the technical ideas of the present invention is given. Among various physical properties of the particulate water-absorbing agent, a liquid absorption speed is directly linked with an absorption speed of a body fluid such as urine, and therefore is an important index greatly related to comfort of a user of an absorbent article. In order to increase the absorption speed of the particulate water-absorbing agent, a generally-employed method increases a specific surface area of the particulate water-absorbing agent.

In accordance with this method, however, a problem often occurs in a surface-crosslinking step in the process for producing the particulate water-absorbing agent. A particulate water-absorbing agent thus obtained tends to have a poor specific re-wet as well as a poor balance between CRC and AAP.

A method for producing a particulate water-absorbing agent in accordance with an aspect of the present invention provides a particulate water-absorbing agent that has a high absorption speed and a reduced specific re-wet. Furthermore, in an embodiment of the present invention, particulate water-absorbing agent provided by the production method has a balance between CRC and AAP within favorable range.

In addition, the particulate water-absorbing agent in accordance with the aspect of the present invention has a high alcohol absorbency. This parameter was found by the inventors of the present invention, and can represent a particulate water-absorbing agent having a high absorption speed and a reduced specific re-wet. That is, the particulate water-absorbing agent in accordance with the aspect of the present invention is a particulate water-absorbing agent having a high absorption speed and a reduced specific re-wet. In an embodiment, the particulate water-absorbing agent also has a balance between CRC and AAP within a favorable range.

Incidentally, as a result of diligent studies, the inventors of the present invention also found that the particulate water-absorbing agent produced to merely have a larger specific surface area is disadvantageous in absorbing time and re-wet amount.

The inventors of the present invention conducted further diligent studies and found it possible to avoid the disadvantages by maintaining a specific re-wet of the particulate water-absorbing agent so as to fall within a certain range. In addition, the inventors of the present invention also found it possible to further improve the disadvantages by maintaining a saline flow conductivity (SFC) so as to fall within a certain range. Furthermore, the inventors of the present invention found that use of a certain surface-crosslinking agent makes it possible to maintain the specific re-wet and the SFC so as to fall within the certain ranges.

[1] Definition of Terms

[1-1] "Water-Absorbing Resin" and "Water-Absorbing Resin Powder"

Herein, the term "water-absorbing resin" refers to a polymer gelling agent having a water-swelling property and a water-insolubility. The water-swelling property and the water-insolubility mean the following physical properties.

Water-swelling property: A CRC (defined in ERT 441.2-02) of not less than 5 g/g.

Water-insolubility: An Ext (defined in ERT 470.2-02) of 50 mass % or less.

The water-absorbing resin can be designed to suit the purpose, and is not limited to any particular kind. The water-absorbing resin is preferably a hydrophilic crosslinked polymer obtained by polymerizing and crosslinking unsaturated monomers each having a carboxyl group. Examples of forms of the water-absorbing resin encompass a sheet, fibers, a film, a particulate form, and a gel. Among these, a particulate water-absorbing resin is suitable for the water-absorbing film in accordance with the embodiment of the present invention.

Herein, the term "water-absorbing resin" is not limited to a resin consisting only of the water-absorbing resin in a total amount (100 mass %). Alternatively, the "water-absorbing resin" may be a water-absorbing resin composition containing an additive and/or the like, as long as the composition has a CRC and an Ext as those described above. In addition, the term "water-absorbing resin" as used herein refers to a concept encompassing an intermediate produced in the production process of the water-absorbing resin, too. For example, the term "water-absorbing resin" may also be used to refer to, e.g., a crosslinked hydrogel polymer produced in a polymerization step, a dried polymer produced in a drying step, and a water-absorbing resin powder which has not been subjected to surface-crosslinking.

Thus, herein, the "water-absorbing resin" is a collective term used to refer not only to the water-absorbing resin itself, but also to a water-absorbing resin composition and an intermediate.

In the present invention, the water-absorbing resins may sometimes be distinguished from one to another according to their crosslinking densities. That is, herein, "a polymer that is crosslinked only in its internal part (i.e., a polymer having an internal part and a surface layer whose crosslinking densities are substantially equal to each other)" and "a polymer that is crosslinked not only in its internal part but also in its surface layer (i.e., a polymer having a surface layer whose crosslinking density is relatively higher than a crosslinking density of an internal part of the polymer)" may sometimes be distinguished from each other. According to the above expressions, the polymer that is crosslinked only in its internal part can be called a "water-absorbing resin powder", whereas the polymer that is crosslinked not only in its internal part but also in its surface layer can be called "water-absorbing resin particles". A particulate water-absorbing agent in accordance with an embodiment of the present invention is preferably a particulate water-absorbing agent containing as a main component a polyacrylic acid (salt)-based resin.

[1-2] "Particulate Water-Absorbing Agent"

The term "water-absorbing agent" as used herein refers to an absorbent gelling agent that contains a water-absorbing resin as a main component and that absorbs a water-based liquid. The "water-based liquid" is not particularly limited and needs not consist only of water, as long as it is a liquid that contains water. Examples of the water-based liquid encompass urine, blood, sweat, excrement, a waste fluid, moisture, vapor, ice, a mixture of water and an organic solvent and/or an inorganic solvent, rainwater, and groundwater. The water-based liquids to be absorbed by the absorbent body according to the embodiment of the present invention are preferably urine, menstrual blood, sweat, and other body fluids.

Herein, the term "particulate water-absorbing agent" refers to a particulate (powdered) water-absorbing agent. The concept "particulate water-absorbing agent" encompasses both a single particle of the particulate water-absorbing agent and a plurality of particles of the particulate water-absorbing agent in aggregate. Herein, "particulate" refers to a substance being in the form of one or more particles. The term "particle" refers to a relatively small piece of a material, having a size of several Å to several mm (see "particle" in "McGraw-Hill Dictionary of Scientific and Technical Terms, Third Edition", edited by editorial board of the McGraw-Hill Dictionary of Scientific and Technical Terms, Nikkan Kogyo Shimbun, 1996, p. 1929). Herein, the "particulate water-absorbing agent" may be simply written as a "water-absorbing agent".

The particulate water-absorbing agent contains as a main component the water-absorbing resin that is a polymer. The particulate water-absorbing agent contains the water-absorbing resin that is a polymer in an amount of 60 mass % to 100 mass %, preferably 70 mass % to 100 mass %, even more preferably 80 mass % to 100 mass %, and still more preferably 90 mass % to 100 mass %. The remainder of the particulate water-absorbing agent may optionally include, for example, water and/or an additive (e.g., inorganic fine particles and/or polyvalent metal cations).

In other words, the upper limit of the amount of water-absorbing resin in the particulate water-absorbing agent, is approximately 100 mass %, 99 mass %, 97 mass %, 95 mass %, or 90 mass %, for example. The particulate water-absorbing agent preferably further includes one or more components other than the water-absorbing resin in an amount of approximately 0 mass % to 10 mass %, in particular water and/or additives (such as inorganic fine particles and/or polyvalent metal cations), for example.

A moisture content in the particulate water-absorbing agent is preferably 0.2 mass % to 30 mass %. As described above, the term "particulate water-absorbing agent" also encompasses a water-absorbing resin composition in which components such as water and/or additives are integrated with the water-absorbing resin.

Examples of the water-absorbing resin to be contained as a main component in the particulate water-absorbing agent encompass a polyacrylic acid (salt)-based resin, a polysulfonic acid (salt)-based resin, a maleic anhydride (salt)-based resin, a polyacrylamide-based resin, a polyvinyl alcohol-based resin, a polyethylene oxide-based resin, a polyaspartic acid (salt)-based resin, a polyglutamic acid (salt)-based resin, a polyalginic acid (salt)-based resin, a starch-based resin, and a cellulose-based resin. The water-absorbing resin is preferably a polyacrylic acid (salt)-based resin.

[1-3] Polyacrylic Acid (Salt)

Herein, the term "polyacrylic acid (salt)" refers to polyacrylic acid and/or a salt thereof. The polyacrylic acid (salt) is a polymer which contains, as a main component, a repeating unit of acrylic acid and/or a salt thereof (hereinafter referred to as "acrylic acid (salt)") and optionally further contains a graft component. The polyacrylic acid (salt) is obtained by, for example, polymerization of acrylic acid (salt), or hydrolysis of e.g., polyacrylamide or polyacrylonitrile. Preferably, the polyacrylic acid is obtained by polymerization of an acrylic acid (salt).

The wording "contains as a main component" means that the amount of the acrylic acid (salt) used when polymerizing polyacrylic acid (salt) is ordinarily 50 mol % to 100 mol %, preferably 70 mol % to 100 mol %, more preferably 90 mol % to 100 mol %, and even more preferably substantially 100 mol %, relative to a total amount of monomers for use in polymerization (excluding an internal crosslinking agent).

The polyacrylic acid is preferably a monovalent salt, more preferably an alkali metallic salt or an ammonium salt, even more preferably an alkali metallic salt, and particularly preferably a sodium salt.

[1-4] "EDANA" and "ERT"

The term "EDANA" is an acronym for the European Disposables and Nonwovens Associations. The term "ERT" is an acronym for EDANA Recommended Test Methods, which are European standard (substantially international standard) measuring methods for water-absorbing resin. Herein, physical properties of water-absorbing resin are measured in conformity with the 2002 version of ERT, unless otherwise specified.

[1-4-1] "CRC (ERT 441.2-02)"

The term "CRC" is an acronym for "centrifuge retention capacity", and means a fluid retention capacity without pressure (herein, the term "fluid retention capacity" is also used) of a particulate water-absorbing agent or a water-absorbing resin. A method for measuring a CRC is outlined below. First, 0.2 g of the particulate water-absorbing agent or water-absorbing resin is put into a nonwoven fabric bag, and is immersed in a large excess of a 0.9 mass % aqueous sodium chloride solution for 30 minutes so as to be swollen freely. Thereafter, the bag is drained with a centrifuge (250G). Then, the mass of the particulate water-absorbing agent or water-absorbing resin is measured, and the fluid retention capacity (unit: g/g) thereof is determined.

[1-4-2] "AAP (ERT 442.2-02)"

The term "AAP" is an acronym for "absorption against pressure", and means a fluid retention capacity under pressure of a particulate water-absorbing agent or a water-absorbing resin. A method for measuring an AAP is outlined below. First, 0.9 g of the particulate water-absorbing agent or water-absorbing resin is swollen with a large excess of a 0.9 mass % aqueous sodium chloride solution for an hour under a load of 2.06 kPa (21 g/cm$^2$, 0.3 psi). Thereafter, the mass of the particulate water-absorbing agent or water-absorbing resin is measured, and the fluid retention capacity (unit: g/g) thereof is determined. The measurement is sometimes carried out under a load of 4.83 kPa (49 g/cm$^2$, 0.7 psi), which is different from the aforementioned load. In the Examples herein, the values under the different load were also measured.

ERT 442.2-02 uses the term "absorption under pressure (AUP)", which means a physical property substantially identical to AAP.

[1-4-3] "PSD (ERT 420.2-02)"

The term "PSD" is an acronym for "particle size distribution", and means a particle size distribution of the particulate water-absorbing agent or the water-absorbing resin, as measured by sieve classification. In relation to this, a mass average particle diameter (D50) and a logarithmic standard deviation (σζ) of the particle size distribution are measured according to methods similar to those disclosed in the Specification of US Patent No. 7638570 (see "(3) Mass-Average Particle Diameter (D50) and Logarithmic Standard Deviation (σζ) of Particle Diameter Distribution" in U.S. Pat. No. 7,638,570).

Herein, unless otherwise specified, the "particle size distribution", "mass average particle diameter (D50)", and "logarithmic standard deviation (σζ) of a particle size distribution" are collectively expressed by the term "PSD" for convenience.

[1-4-4] "Ext (ERT 470.2-02)"

The term "Ext" is an acronym for "extractables", and means a water-soluble content (an amount of a water-soluble content) in the water-absorbing resin. A method for measuring the Ext is outlined below. First, 1.0 g of the water-absorbing resin is added to 200 mL of a 0.9 mass % aqueous sodium chloride solution, and the resultant is stirred at 500 rpm for 16 hours. Then, the amount of dissolved polymer is measured by pH titrimetric method (unit: mass %).

[1-5] Liquid Permeability

Herein, the "liquid permeability" of the water-absorbing resin refers to flowability of a liquid passing between the swollen gel particles under load or without load. One representative technique for measuring the "liquid permeability" is a saline flow conductivity (SFC).

The SFC indicates a liquid permeability of a 0.69 mass % aqueous sodium chloride solution with respect to 1.5 g of the water-absorbing resin under a load of 2.1 kPa. The SFC is measured in accordance with the SFC test method described in U.S. Pat. No. 5,669,894.

[1-6] Others

Herein, a range "X to Y" means "not less than X and not more than Y".

Herein, unless otherwise specified, the unit of mass "t (ton)" means "metric ton". "Ppm" means "ppm by mass". The following term pairs are considered to be synonymous: "mass" and "weight"; "parts by mass" and "parts by weight"; "mass %" and "weight %"; and "ppm by mass" and "ppm by weight".

Herein, the term " . . . acid (salt)" means " . . . acid and/or a salt thereof". The term "(meth)acrylic" means "acrylic and/or methacrylic".

Herein, the unit of volume "liter" may be denoted as "l" or "L". "Mass %" may be denoted as "wt %". In measurements of trace components, values equal to or less than a detection limit are indicated as N.D. (Non Detected).

[2] Physical Properties of Particulate Water-Absorbing Agent

The water-absorbing agent (for example, the particulate water-absorbing agent obtained by the production method in accordance with the aspect of the present invention) in accordance with the aspect of the present invention satisfies the conditions described in [2-1] and [2-2] below. In a case where the particulate water-absorbing agent is applied to an absorbent article (particularly, a paper diaper), it is desirable that, among the physical properties described in [2-3] to [2-9], preferably at least one or more, more preferably two or more including the AAP, even more preferably three or more including the AAP, still more preferably four or more including the AAP, yet more preferably five or more including the AAP, particularly preferably six or more including the AAP, and most preferably all the properties be controlled so as to fall within desired range(s).

Unless otherwise specified, the physical properties described below are measured in accordance with EDANA method.

[2-1] Specific Surface Area Index

The particulate water-absorbing agent in accordance with the embodiment of the present invention has a specific surface area index expressed by formula (1a) below, the specific surface area index being not less than 1.5, preferably not less than 1.6, and more preferably not less than 1.7.

$$\text{(Specific surface area index)} = \text{(specific surface area of particulate water-absorbing agent)}/(10^8 \times D50^2) \quad (1a).$$

In formula (1a), the unit of the specific surface area index is [1/kg]. The unit of the specific surface area is [m$^2$/kg]. D50 denotes a mass average particle diameter, and the unit of D50 is [m] (it should be noted that the unit of D50 in formula (1a) is [m], although the technical field to which the present invention pertains often uses [μm] as the unit of D50).

Herein, the specific surface area is measured by an X-ray CT method. A specific method for measuring the specific surface area is as described in the items of the Examples.

The specific surface area index expressed by formula (1a) is obtained by standardizing the specific surface area of the entire particulate water-absorbing agent by the square of the mass average particle diameter. Generally, a surface area of a particle having an uneven surface (i.e., an uneven particle) is larger than a surface area of a spherical particle having a diameter identical to that of the uneven particle (pi×the square of a particle diameter). Thus, the degree of unevenness of the surface of the particle can be expressed by dividing the surface area of the uneven particle by the surface area of the spherical particle having the diameter identical to that of the uneven particle. The above-described specific surface area index is obtained by dividing the specific surface area of the whole of the particulate water-absorbing agent (corresponding to the surface area of the uneven particle) by the square of the mass average particle diameter (corresponding to the surface area of the spherical particle having the diameter identical to that of the uneven particle). Therefore, by this index, it is possible to express the degree of unevenness of the surface of the water-absorbing resin particle.

In addition, with the specific surface area index, particulate water-absorbing agents having different particle size distributions or different mass average particle diameters (e.g., a particulate water-absorbing agent of D50=300 μm and a particulate water-absorbing agent of D50=450 μm) can be compared to each other in terms of the degrees of unevenness of the particle surface. A particulate water-absorbing agent having a larger specific surface area index tends to have a larger effective surface area (a larger surface area contributing to an improvement in water-absorbing property) and a higher absorption speed (e.g., a Vortex).

In a measurement of a specific surface area index, expressed by formula (1a), of a particulate water-absorbing agent used in an absorbent article such as a paper diaper, a subject to be measured is the particulate water-absorbing agent taken out from the absorbent article. In taking out of the particulate water-absorbing agent from the absorbent article, particulate water-absorbing agent having a small particle size is hardly taken out. Consequently, the particle size distribution tends to change as a whole. However, even when the particle size distribution has changed, the specific surface area index expressed by formula (1a) would have a substantially constant value.

In addition, in the later-described production process of the particulate water-absorbing agent, the specific surface area and the mass average particle diameter of the particulate water-absorbing agent (water-absorbing resin powder) remain almost unchanged before and after a surface-crosslinking step. Thus, the specific surface area index expressed by formula (1a) and the specific surface area index expressed by the later-described formula (1) have substantially identical values. Therefore, herein, "a specific surface area index of a particulate water-absorbing agent" and "a specific surface area index of a water-absorbing resin powder" are interchangeable with each other.

The specific surface area index can be controlled by, e.g., introduction of a surfactant and/or a blowing agent into a monomer solution in a polymerization step, adjustment of a gel-crushing condition(s) in a gel-crushing step, and/or adjustment of a particle size of powder in a granulation step and/or a sizing step. The introduction of the surfactant and/or the blowing agent and the adjustment of the gel-crushing condition(s) will be described in detail later.

There is no particular limitation on the upper limit of the specific surface area index. However, considering productivity in the production process and physical property balance of a particulate water-absorbing agent to be obtained, the specific surface area index is suitably 3 or less, and more preferably 2.5 or less. With the specific surface area index higher than 3, various properties (e.g., liquid permeability) of the particulate water-absorbing agent may possibly be deteriorated, which may lead to collapsing of the physical property balance in the particulate water-absorbing agent as a whole.

[2-2] Alcohol Absorbency Parameter

The particulate water-absorbing agent in accordance with the embodiment of the present invention has an excellent alcohol absorbency. Specifically, a proportion of a CRC of the particulate water-absorbing agent measured with use of a 35 mass % aqueous ethanol solution with respect to the CRC (CRC (35% EtOH)/CRC) is not less than 1.2, preferably not less than 1.3, more preferably not less than 1.4, and even more preferably not less than 1.5. A proportion of a CRC of the particulate water-absorbing agent measured with use of a 60 mass % aqueous 1,2-propylene glycol solution with respect to the CRC (CRC (60% PG)/CRC) is not less than 0.40, preferably not less than 0.45, more preferably not less than 0.50, and even more preferably not less than 0.55.

There is no particular limitation on the upper limit of the alcohol absorbency parameter. Considering balance between the alcohol absorbency parameter and other physical properties, it is suitable that CRC (35% EtOH)/CRC is set at 5.0 or less and CRC (60% PG)/CRC is set at 1.0 or less.

A specific method for measuring the CRC (35% EtOH) and the CRC (60% PG) is as described in the items of the Examples. The alcohol absorbency (CRC (35% EtOH) and CRC (60% PG)) itself of the particulate water-absorbing agent is affected by the water absorbing ability (CRC) of the particulate water-absorbing agent. Therefore, herein, a value obtained by standardizing the alcohol absorbency parameter with the CRC is used for evaluation.

[2-3] SFC

The particulate water-absorbing agent in accordance with the embodiment of the present invention has a SFC (saline flow conductivity) (unit: $\times 10^{-7} \cdot cm^3 \cdot s \cdot g^{-1}$) of not less than 5, preferably not less than 10, and more preferably not less than 15. The upper limit of the SFC is preferably 200 or less, and more preferably 150 or less.

A particulate water-absorbing agent having a SFC of less than 5 has a low permeability of liquid such as urine, blood, and/or the like, and therefore is not suitably applied to an absorbent article such as a paper diaper. Meanwhile, a particulate water-absorbing agent having a SFC exceeding 200 may possibly cause a liquid leakage due to insufficient absorption of urine, blood, and/or the like, and therefore is not suitably applied to an absorbent article such as a paper diaper. It is possible to control the SFC by selecting a particle size, a surface-crosslinking agent, a polyvalent metal salt, and/or a cationic polymer, for example.

[2-4] CRC

The particulate water-absorbing agent in accordance with the embodiment of the present invention has a CRC (centrifuge retention capacity) of ordinarily not less than 5 g/g, preferably 10 g/g to 100 g/g, more preferably 15 g/g to 80 g/g, even more preferably 20 g/g to 45 g/g, and particularly preferably 25 g/g to 40 g/g.

A particulate water-absorbing agent having a CRC of less than 5 g/g has a low absorbency, and is not suitably applied to an absorbent article such as a paper diaper. Meanwhile, a particulate water-absorbing agent having a CRC exceeding 100 g/g has a lowered absorption speed of urine, blood, and/or the like, and therefore is not suitably applied to a high-absorption-speed type paper diaper. That is, a particulate water-absorbing agent having a CRC within the above range achieves excellent absorbing ability of urine and/or the like, and therefore is suitably applied to an absorbent article such as a paper diaper. It is possible to control the CRC by selecting an internal crosslinking agent and/or a surface-crosslinking agent, for example.

[2-5] AAP-2.1 kPa and AAP-4.8 kPa

The particulate water-absorbing agent in accordance with the embodiment of the present invention has an AAP-2.1 kPa (fluid retention capacity under pressure) of preferably 10 g/g to 100 g/g, more preferably 15 g/g to 80 g/g, even more preferably 20 g/g to 45 g/g, and particularly preferably 25 g/g to 40 g/g.

The particulate water-absorbing agent in accordance with the embodiment of the present invention has an AAP-4.8 kPa (fluid retention capacity under pressure) of preferably 5 g/g to 80 g/g, more preferably 10 g/g to 50 g/g, even more preferably 15 g/g to 40 g/g, and particularly preferably 20 g/g to 35 g/g.

A particulate water-absorbing agent having an AAP-2.1 kPa of less than 10 g/g and an AAP-4.8 kPa of less than 5 g/g allows an increased amount of the liquid (re-wet) to go outside again when a pressure is applied to an absorbent body, and therefore is not suitably applied to an absorbent article such as a paper diaper. On the contrary, a particulate water-absorbing agent having an AAP-2.1 kPa and/or AAP-4.8 kPa within the above range(s) achieves excellent ability of absorbing urine and/or the like, and therefore is suitably applied to an absorbent article such as a paper diaper.

Herein, the expression simply written as "AAP" refers to both AAP-2.1 kPa and AAP-4.8 kPa.

Incidentally, there is suitable balance between the CRC and the AAP. That is, a particulate water-absorbing agent having a CRC and an AAP not only being within the above-described suitable numerical ranges but also being in a certain relation can be said as a particulate water-absorbing agent having a more preferable physical property. Specifically, the value of the AAP-2.1 kPa (g/g) is preferably higher than the value of the CRC (g/g). The particulate water-absorbing agent having such physical properties can exhibit excellent absorbing ability either under pressure or without pressure.

[2-6] Vortex

The particulate water-absorbing agent in accordance with the embodiment of the present invention preferably has a Vortex (water absorption speed) of 50 seconds or less, more preferably 47 seconds or less, even more preferably 45 seconds or less, and particularly preferably 40 seconds or less.

A particulate water-absorbing agent having a Vortex within the above range achieves excellent absorbing ability of urine and/or the like, and therefore is suitably applied to an absorbent article such as a paper diaper. A particulate water-absorbing agent having a Vortex within the above range can be evaluated as having a sufficiently "high water absorption speed" even in comparison to conventional particulate water-absorbing agents.

[2-7] Ext

The particulate water-absorbing agent in accordance with the embodiment of the present invention has an Ext (water-soluble content) of ordinarily 50 mass % or less, preferably 35 mass % or less, more preferably 25 mass % or less, even more preferably 20 mass % or less, and particularly preferably 15 mass % or less. From the viewpoint of balance between the Ext and other physical properties, the lower limit of the Ext is preferably 0 mass %, and more preferably approximately 0.1 mass %.

A particulate water-absorbing agent having an Ext exceeding 50 mass % may possibly have a low gel strength and poor liquid permeability. Furthermore, the particulate water-absorbing agent having the Ext exceeding 50 mass % has an increased re-wet, and therefore is not suitably applied to an absorbent article such as a paper diaper. Conversely, a particulate water-absorbing agent having an Ext within the above range achieves excellent performance of dispersing a body fluid such as urine over the entire absorbent body, and therefore is suitably applied to absorbent articles such as a paper diaper. It is possible to control the Ext by selecting an internal crosslinking agent and/or the like.

[2-8] PSD

The particulate water-absorbing agent in accordance with the embodiment of the present invention is preferably controlled so as to have a PSD (a particle size distribution, a mass average particle diameter (D50), and a logarithmic standard deviation ($\sigma\zeta$) of particle size distribution) within the following ranges.

For the particle size distribution, a content of particles having a particle diameter of not less than 150 μm and less than 850 μm is preferably not less than 90 mass %, more preferably not less than 95 mass %, and even more preferably not less than 97 mass %.

A content of particles having a particle diameter of less than 150 μm is preferably 5 mass % or less, more preferably 3 mass % or less, even more preferably 2 mass % or less, and particularly preferably 1 mass % or less. A content of particles having a particle diameter of not less than 850 μm is preferably 5 mass % or less, more preferably 3 mass % or less, and even more preferably 1 mass % or less. Each of the lower limit of the content of the particles having a particle diameter of less than 150 μm and the lower limit of the content of the particles having a particle diameter of not less than 850 μm is preferably as low as possible, and is preferably 0 mass %. Alternatively, each lower limit may be approximately 0.1 mass %.

The mass average particle diameter (D50) is preferably 200 μm to 600 μm, more preferably 250 μm to 550 μm, even more preferably 275 μm to 550 μm, still more preferably 275 μm to 500 μm, and particularly preferably 300 μm to 500 μm.

The logarithmic standard deviation ($\sigma\zeta$) of the particle size distribution is preferably 0.20 to 0.50, more preferably 0.25 to 0.45, even more preferably 0.25 to 0.40, and particularly preferably 0.25 to 0.35.

A particulate water-absorbing agent having a PSD within the above ranges improves the touch of an absorbent article and achieves excellent performance of dispersing a body fluid such as urine over the entire absorbent body, and therefore is suitably applied to an absorbent article such as a paper diaper.

[2-9] Specific Re-Wet

The particulate water-absorbing agent in accordance with the embodiment of the present invention has a specific re-wet of 3.7 g or less, preferably 3.4 g or less, and more preferably 3.0 g or less. A particulate water-absorbing agent having a specific re-wet within the above range can retain a liquid that has been once retained in its inside or between the particles even when a load is applied, and therefore is suitably applied to an absorbent article such as a paper diaper.

The specific re-wet is a value indicating an ability of a particulate water-absorbing agent to retain a liquid under pressure. As will be described later, in a measurement of a specific re-wet, a particulate water-absorbing agent is allowed to be swollen as it is. Therefore, unlike a re-wet amount and/or the like measured on an absorbent body having been produced, the specific re-wet enables evaluation of the performance (load resistance and liquid retention ability) of the particulate water-absorbing agent itself. The particulate water-absorbing agent in accordance with the embodiment of the present invention has a high gel strength, and keeps the forms of the particles (the particles are not crushed) even when being subjected to a pressure after being swollen. Thus, the particulate water-absorbing agent has a low specific re-wet.

It should be noted that the specific re-wet value is affected also by the liquid permeability. Specifically, a particulate water-absorbing agent having a high liquid permeability tends to have a high specific re-wet value. Therefore, a comparison in terms of the specific re-wet values is effective only between particulate water-absorbing agents having almost same degrees of liquid permeability.

The particulate water-absorbing agent in accordance with the embodiment of the present invention has an SFC as high as not less than $5\times10^{-7} \cdot cm^3 \cdot s \cdot g^{-1}$ and a specific re-wet controlled so as to be 3.7 g or less (i.e., a specific re-wet of 3.7 g or less and a saline flow conductivity (SFC) of not less than $5\times10^{-7} \cdot cm^3 \cdot s \cdot g^{-1}$). The particulate water-absorbing agent preferably has an SFC of not less than $5\times10^{-}$ 7·cm³·s·g⁻¹ and a specific re-wet of 3.4 g or less, and more preferably a specific re-wet of 3.0 g or less. Even more preferably, the particulate water-absorbing agent has an SFC of not less than 10×10⁻⁷·cm³·s·g⁻¹ and a specific re-wet of 3.4 g or less, and more preferably, a specific re-wet of 3.0 g or less. Particularly preferably, the particulate water-absorbing agent has an SFC of not less than 15×10⁻⁷·cm³·s·g⁻¹ and a specific re-wet of 3.4 g or less. Most preferably, the particulate water-absorbing agent has a specific re-wet of 3.0 g or less. A particulate water-absorbing agent having a specific re-wet and an SFC within the above ranges achieves excellent liquid permeability, and is suitably applied to an absorbent article such as a paper diaper.

It is possible to measure a specific re-wet by a method described in Japanese Patent Application Publication, Tokukai, No. 2015-066009 (more specifically, see the Examples of the present application).

[3] Method for Producing Particulate Water-Absorbing Agent

The method for producing the particulate water-absorbing agent in accordance with the embodiment of the present invention includes the step of surface-crosslinking a water-absorbing resin powder with use of a surface-crosslinking agent, wherein the water-absorbing resin powder has a specific surface area index of not less than 1.5, the specific surface area index being expressed by formula (1) below, and the surface-crosslinking agent has an apparent Hansen solubility parameter of 22.5 MPa$^{1/2}$ to 28.5 MPa$^{1/2}$.

$$\text{(Specific surface area index)} = \text{(specific surface area of water-absorbing resin powder)}/(10^8 \times D50^2) \quad (1).$$

The method for producing the particulate water-absorbing agent in accordance with another aspect of the present invention includes the step of surface-crosslinking a water-absorbing resin powder with use of a surface-crosslinking agent, wherein the water-absorbing resin powder has a specific surface area index of not less than 1.5, the specific surface area index being expressed by formula (1) below, and the surface-crosslinking agent contains a $C_{6-8}$ polyhydric alcohol.

$$\text{(Specific surface area index)} = \text{(specific surface area of water-absorbing resin powder)}/(10^8 \times D50^2) \quad (1).$$

In formula (1), the unit of the specific surface area index is [1/kg]. The unit of the specific surface area is [m²/kg]. D50 denotes a mass average particle diameter, and the unit of D50 is [m] (it should be noted that the unit of D50 in formula (1) is [m], although the technical field to which the present invention pertains often uses [μm] as the unit of D50).

The following will sequentially describe the steps in the method for producing the particulate water-absorbing agent in accordance with the embodiment of the present invention.

[3-1] Step of Preparing Aqueous Monomer Solution

This step is a step of preparing an aqueous solution containing a monomer (e.g., an acrylic acid (salt)) as a main component (this aqueous solution is hereinafter referred to as an "aqueous monomer solution"). Note that a monomer slurry liquid may be used instead as long as the water-absorbing resin obtained does not have degraded water absorption performance. For convenience of description, however, an aqueous monomer solution is described here.

The wording "contains as a main component" means that the amount of the acrylic acid (salt) used to polymerize polyacrylic acid (salt) is ordinarily 50 mol % to 100 mol %, preferably 70 mol % to 100 mol %, more preferably 90 mol % to 100 mol %, and even more preferably substantially 100 mol %, relative to a total amount of monomers for use in polymerization (excluding an internal crosslinking agent).

(Acrylic Acid (Salt))

In this step, it is preferable that an acrylic acid and/or a salt thereof (hereinafter referred to as "acrylic acid (salt)") be used as a monomer, from the viewpoint of physical properties of the particulate water-absorbing agent to be produced, and from the viewpoint of productivity.

The acrylic acid is a known acrylic acid containing a small amount of a component such as a polymerization inhibitor and/or an impurity. The polymerization inhibitor is preferably methoxyphenol, and more preferably p-methoxyphenol. The acrylic acid contains the polymerization inhibitor in a content of preferably 200 ppm or less, more preferably 10 ppm to 160 ppm, even more preferably 20 ppm to 100 ppm, from the viewpoints of the polymerizability of the acrylic acid and the color of the particulate water-absorbing agent to be obtained, for example. Examples of the impurity encompass organic compounds (e.g., an acetic acid, a propionic acid, and furfural) as well as compounds disclosed in U.S. Patent Application Publication No. 2008/0161512.

The acrylic acid salt is obtained by neutralizing the acrylic acid with use of a basic composition. The acrylic acid salt may be a commercially available acrylic acid salt (such as sodium acrylate) or may be obtained in the production process of the particulate water-absorbing agent.

The "basic composition" in this step refers to a composition containing a basic compound. Examples of the basic compound encompass: a carbonate, bicarbonate, or hydroxide of an alkali metal; ammonia; and organic amine. Of these, a basic composition having strong basicity is preferable from the viewpoint of the physical properties of the particulate water-absorbing agent to be obtained. As such, the basic compound is preferably a hydroxide of alkali metal (such as sodium hydroxide, potassium hydroxide, or lithium hydroxide), and is more preferably sodium hydroxide.

In order to neutralize acrylic acid to obtain acrylic acid (salt), acrylic acid may be neutralized prior to polymerization, or a crosslinked hydrogel polymer obtained by polymerizing and crosslinking acrylic acid may be neutralized (hereinafter, the latter is referred to as "later neutralization"). In order to obtain the acrylic acid (salt), neutralization before polymerization and later neutralization may be used in combination. The step of neutralization is not limited to any particular type, and may be of a continuous type or a batch type. However, the continuous type is preferable from the viewpoint of production efficiency and the like.

With regard to conditions such as the apparatus used for neutralization, a neutralization temperature, and a retention time, the conditions disclosed in International Publication No. WO 2009/123197 and U.S. Patent Application Publication No. 2008/0194863 can be applied.

The neutralization rate of the acrylic acid (salt) is preferably 10 mol % to 90 mol %, more preferably 40 mol % to 85 mol %, even more preferably 50 mol % to 80 mol %, and particularly preferably 60 mol % to 75 mol %, relative to acid groups of a monomer. A neutralization rate that is less than 10 mol % may result in a significant decrease in fluid retention capacity. With a neutralization rate that is higher than 90 mol %, it may not be possible to obtain a water-absorbing resin having a high fluid retention capacity under pressure.

The expression "a neutralization rate of 75 mol %" of the acrylic acid (salt) means a mixed state of 25 mol % acrylic acid and 75 mol % acrylic acid salt. Such a mixture may be written as a "partially neutralized acrylic acid product".

The neutralization rate described above is also suitable for a case where later neutralization is carried out. In addition, the neutralization rate described above is suitably applied also to a numerical range of a neutralization rate for the particulate water-absorbing agent.

(Other Monomer(s))

The "other monomer(s)" in this step refer to monomers other than the acrylic acid (salt). The particulate water-absorbing agent can be produced with use of acrylic acid (salt) and other monomer(s) in combination. Examples of the other monomer(s) encompass an unsaturated monomer which is water-soluble or hydrophobic. As a more specific example, the compounds disclosed in U.S. Patent Application Publication No. 2005/0215734 (excluding acrylic acid) may be used.

In the case where other monomer(s) is used, the amount of other monomer(s) is preferably 30 mol % or less, more preferably 10 mol % or less, and even more preferably 5 mol % or less, relative to the total amount (100 mol %) of monomers (excluding the internal crosslinking agent).

(Internal Crosslinking Agent)

For an internal crosslinking agent used to produce the particulate water-absorbing agent, the compounds disclosed in U.S. Pat. No. 6,241,928 may be used. From these compounds, one or more kinds of compounds are selected in consideration of reactivity.

The amount of internal crosslinking agent used is preferably 0.0001 mol % to 10 mol %, and more preferably 0.001 mol % to 1 mol %, relative to the total amount of monomers. Setting the used amount to fall within the above range makes it possible to obtain a desired water-absorbing resin. If the used amount is too small, there tends to be a decrease in gel strength and an increase in a water-soluble content, which is not preferable. Conversely, if the used amount is too great, there tends to be a decrease in the fluid retention capacity, which is not preferable.

The internal crosslinking agent is preferably used in the following manner. That is, a certain amount of the internal crosslinking agent is added in advance to an aqueous monomer solution, and then polymerization and a crosslinking reaction are carried out simultaneously. Other example methods that may be employed encompass the following: (i) a method in which an internal crosslinking agent is added during or after the polymerization so that post-crosslinking is carried out; (ii) a method in which radical crosslinking is carried out with use of a radical polymerization initiator; and (iii) a method in which radiation crosslinking is carried out with use of active energy rays such as an electron ray or an ultraviolet ray. These methods may be used in combination.

(Surfactant and Blowing Agent)

The method for producing the water-absorbing resin in accordance with the aspect of the present invention uses a water-absorbing resin powder having a specific surface area index of not less than 1.5. One example of the method for producing the water-absorbing resin powder may be a method in which a surfactant and/or a blowing agent is added to a monomer solution. As a result of foaming of the surfactant and/or blowing agent in the monomer solution, the specific surface area of the water-absorbing resin powder increases, so that the specific surface area index of the water-absorbing resin powder can be not less than 1.5.

Examples of the surfactant encompass polyoxyethylene (20) sorbitan monostearate, polyoxyethylene lauryl ether, and polyoxyethylene oleyl ether. Examples of the blowing agent encompass carbonates (such as sodium hydrogen carbonate and ammonium carbonate), azo compounds (such as 2,2'-azobisisobutyronitrile and 2,2'-azobis-2-methylbutyronitrile), and air bubbles. In order to obtain a water-absorbing resin powder having a specific surface area index of not less than 1.5, the surfactant and/or the blowing agent may be added in an amount of more than 0 and 0.1 mass % or less relative to the total amount of the monomer.

(Other Substances Added to Aqueous Monomer Solution)

In order to improve the physical properties of the resulting water-absorbing resin, other substances may be added in the step of preparing the aqueous monomer solution.

Examples of other substances encompass hydrophilic polymers (such as starch, a starch derivative, cellulose, a cellulose derivative, polyvinyl alcohol, polyacrylic acid (salt), and crosslinked polyacrylic acid (salt)). The added amount of the hydrophilic polymer is preferably 50 mass % or less, more preferably 20 mass % or less, even more preferably 10 mass % or less, and particularly preferably 5 mass % or less (the lower limit is 0 mass %), relative to the total amount of the monomer.

In addition to the hydrophilic polymer, a chelating agent, a chain transfer agent, and/or the like may be added. The added amount of these substance(s) is preferably 5 mass % or less, more preferably 1 mass % or less, and even more preferably 0.5 mass % or less (the lower limit is 0 mass %), relative to the total amount of the monomer.

The other substance(s) described as examples may be added to the aqueous monomer solution, to an intermediate during polymerization, or to both.

If a water-soluble resin or a water-absorbing resin is used as the hydrophilic polymer, a graft polymer or a water-absorbing resin composition (for example, a polymer produced from starch and an acrylic acid or a polymer produced from PVA and an acrylic acid) can be obtained.

(Monomer Component Concentration)

In this step, the aqueous monomer solution is prepared by adding each of the above mentioned substances to water.

The concentration of the monomer component in the aqueous monomer solution is not particularly limited. However, considering the physical properties of the water-absorbing resin, the concentration of the monomer component is preferably 10 mass % to 80 mass %, more preferably 20 mass % to 75 mass %, and even more preferably 30 mass % to 70 mass %.

The "concentration of the monomer component" is a value obtained by formula (4) below. Note that the "mass of the aqueous monomer solution" in formula (4) does not include the mass of the graft component, the mass of the water-absorbing resin, or the mass of a solvent in reversed phase suspension polymerization other than water.

Monomer component concentration[mass %]=(mass of monomer component/mass of aqueous monomer solution)×100     (4).

If the method of polymerization employed is aqueous solution polymerization or reversed phase suspension polymerization, solvents other than water can be used in combination. The type of the solvent used is not limited to any particular one.

[3-2] Polymerization Step

This step is a step of polymerizing an acrylic acid (salt)-based aqueous monomer solution obtained in the step of preparing the aqueous monomer solution, so that a crosslinked hydrogel polymer (hereinafter referred to as "hydrogel") is obtained.

(Polymerization Initiator)

A polymerization initiator used in this step is selected as appropriate in accordance with e.g. the polymerization method, and is not particularly limited. Examples of the polymerization initiator encompass a pyrolytic-type polymerization initiator, a photolytic-type polymerization initiator, and a redox-type polymerization initiator (a polymerization initiator in combination with a reducing agent, which facilitates decomposition of a pyrolysis-type polymerization initiator and/or a photolytic-type polymerization initiator). Specifically, one or more of the polymerization initiators disclosed in U.S. Pat. No. 7,265,190 can be used as the polymerization initiator. From the viewpoint of the handleability of the polymerization initiator and the physical properties of the obtained particulate water-absorbing agent or water-absorbing resin, the polymerization initiator is preferably a peroxide or an azo compound, more preferably a peroxide, and even more preferably a persulfate.

The amount of the polymerization initiator to be used is preferably 0.001 mol % to 1 mol %, and more preferably 0.001 mol % to 0.5 mol %, relative to the total amount of the monomer. In a case where the redox-type polymerization initiator is used, the amount of the reducing agent to be used is preferably 0.0001 mol % to 0.02 mol % relative to the total amount of the monomer.

Note that the polymerization initiator may not be used. Instead, a polymerization reaction may be initiated by emission of an active energy ray (such as a radial ray, an electron ray, or an ultraviolet ray). Alternatively, the polymerization reaction may be initiated by the polymerization initiator and the active energy ray used in combination.

(Form of Polymerization)

The polymerization method used in this step is not limited to any particular one. However, from the viewpoints of e.g. the water-absorbing property (particularly, liquid permeability) of the particulate water-absorbing agent to be obtained and the ease of polymerization control, the polymerization method is preferably droplet polymerization, aqueous solution polymerization, or reversed phase suspension polymerization, more preferably the aqueous solution polymerization or the reversed phase suspension polymerization, and even more preferably the aqueous solution polymerization. For the aqueous solution polymerization, continuous aqueous solution polymerization is particularly preferable. The continuous aqueous solution polymerization may be continuous belt polymerization or continuous kneader polymerization.

More specific examples of the continuous belt polymerization are disclosed in U.S. Pat. Nos. 4,893,999, 6,241,928, and U.S. Patent Application Publication No. 2005/215734, for example. More specific examples of the continuous kneader polymerization are disclosed in U.S. Pat. Nos. 6,987,151 and 6,710,141, for example. By adopting such continuous aqueous solution polymerization, it is possible to enhance the efficiency in production of the water-absorbing resin.

Preferred modes of the continuous aqueous solution polymerization encompass "high-temperature initiated polymerization" and "high-concentration polymerization".

The "high-temperature initiated polymerization" refers to a method in which polymerization is initiated with the aqueous monomer solution having a temperature of preferably not less than 30° C., more preferably not less than 35° C., even more preferably not less than 40° C., and particularly preferably not less than 50° C. (the upper limit is a boiling point of the aqueous monomer solution). The "high-concentration polymerization" refers to a method in which polymerization is carried out with a monomer concentration of preferably not less than 30 mass %, more preferably not less than 35 mass %, even more preferably not less than 40 mass %, and particularly preferably not less than 45 mass % (the upper limit is a saturated concentration). In this step, it is possible to make the polymerization proceed so as to satisfy both the condition of the high-temperature initiated polymerization and the condition of the high-concentration polymerization.

This step may be carried out in the air atmosphere. However, from the viewpoint of the color of the water-absorbing resin to be obtained, the polymerization is preferably carried out in inert gas (e.g., nitrogen or argon) atmosphere. In this case, an oxygen concentration in the atmosphere is preferably controlled so as to be 1 volume % or less. Furthermore, dissolved oxygen in the aqueous monomer solution is preferably replaced with an inert gas. In this case, the dissolved oxygen concentration is preferably controlled so as to be less than 1 mg/L.

In this step, foaming polymerization may be carried out. The foaming polymerization is carried out by dispersing bubbles (such as an inert gas) in the aqueous monomer solution. For example, air bubbles may be dispersed by a method in which a gas dissolved in the aqueous monomer solution is dispersed by decreasing the solubility, a method in which a gas is introduced from the outside, or a method in which a blowing agent is added to the aqueous monomer solution. In the method in which the gas is introduced from the outside, the gas to be introduced may be oxygen, air, nitrogen, a carbonic acid gas, ozone, or a mixture gas thereof. The gas to be introduced is preferably an inert gas such as nitrogen or a carbonic acid gas. From the viewpoint of the polymerizability and cost, a nitrogen gas is preferable.

In this step, the solid content concentration may be increased during the polymerization. The degree of the increase in the solid content, which is an index indicating the increase in the solid content concentration, is defined by formula (5) below. The degree of the increase in the solid content concentration is preferably not less than 1 mass %, and more preferably not less than 2 mass %.

Degree of increase in solid content[mass %]=solid content concentration of hydrogel after polymerization[mass %]−solid content concentration of aqueous monomer solution [mass %]     (5).

The "solid content concentration of aqueous monomer solution" in formula (5) is a value obtained by formula (6) below.

Solid content concentration of aqueous monomer solution [mass %]={mass of(monomer component+graft component+water-absorbing resin+other solid component(s))/mass of components in polymerization system}×100     (6).

The "components in polymerization system" in formula (6) are the aqueous monomer solution, the graft component, the water-absorbing resin, and other solid component(s) (e.g., water-insoluble fine particles). The "components in polymerization system" do not include a hydrophobic solvent in reversed phase suspension polymerization.

[3-3] Gel-Crushing Step

This step is a step of gel-crushing, with use of, e.g., a screw extruder (such as a kneader or a meat chopper) or a gel-crusher (such as a cutter mill), a hydrogel obtained in the polymerization step in order to obtain a hydrogel in the form of particles (hereinafter referred to as "particulate hydrogel"). If kneader polymerization is employed in the polymerization step, the polymerization step and the gel-crushing step proceed simultaneously. In a case where a polymerization method (e.g., vapor phase polymerization or reversed phase suspension polymerization) in which the particulate hydrogel is obtained directly in the process of polymerization is employed, the gel-crushing step may be omitted.

In order to set the specific surface area index of the particulate water-absorbing agent in accordance with the embodiment of the present invention so as to fall within a suitable range, it is preferable to carry out the gel-crushing step under the following conditions.

(Gel-Grinding Energy)

The upper limit of a gel grinding energy (GGE) required for gel-crushing of the hydrogel per unit weight is preferably 60 J/g or less, more preferably 50 J/g or less, and even more preferably 40 J/g or less. Meanwhile, the lower limit of the gel grinding energy (GGE) is preferably not less than 15 J/g, more preferably not less than 17 J/g, and even more preferably not less than 20 J/g.

Controlling the GGE so as to fall within the above-described range makes it possible to carry out gel-crushing while applying a suitable shearing force and a suitable compressive force to the hydrogel. Note that the GGE is calculated so as to include an energy of a gel-crusher that is idle-running.

Note that the upper limit of a gel grinding energy (2) (GGE (2); also referred to as a net gel grinding energy) not including the energy of the gel-crusher that is idle-running is preferably 40 J/g or less, more preferably 35 J/g or less, and even more preferably 33 J/g or less. Meanwhile, the lower limit of the GGE(2) is preferably 6 J/g or greater, more preferably 9 J/g or greater, and even more preferably 12 J/g or greater.

Controlling the GGE(2) so as to fall within the above-described range makes it possible to carry out gel-crushing while applying a suitable shearing force and a suitable compressive force to the hydrogel.

Note that the GGE and the GGE(2) can be obtained by the method described in International Publication No. WO 2011/126079.

(Moisture Content)

The moisture content of the hydrogel is preferably not less than 40 mass %, and more preferably not less than 45 mass %. Setting the moisture content to fall within the above range makes it possible to yield a particulate water-absorbing agent having excellent physical properties.

The moisture content of the hydrogel can be measured in accordance with EDANA method (ERT 430.2-02). However, since the hydrogel has a relatively large water content, the drying time in the measurement herein is changed to 24 hours.

[3-4] Drying Step

This step is a step of drying the particulate hydrogel obtained in the polymerization step and/or the gel-crushing step until a desired resin solid content is attained, so as to obtain a dried polymer. The resin solid content is calculated from a drying loss of the water-absorbing resin (i.e., a change in mass after heating 1 g of the water-absorbing resin at 180° C. for three hours). The dry solid content of the water-absorbing resin (particulate water-absorbing agent) is preferably not less than 80 mass %, more preferably 85 mass % to 99 mass %, even more preferably 90 mass % to 98 mass %, and particularly preferably 92 mass % to 97 mass %.

The method of drying the particulate hydrogel is not particularly limited. Examples of the drying method encompass thermal drying, hot air drying, drying under reduced pressure, fluidized bed drying, infrared drying, microwave drying, drum dryer drying, drying by azeotropic dehydration with a hydrophobic organic solvent, and high humidity drying by use of high temperature water vapor. Among these examples, from the viewpoint of drying efficiency, the drying method is preferably hot air drying, and more preferably band drying (hot air drying which is performed on a through-flow belt).

The drying temperature in this step is preferably 120° C. to 250° C., more preferably 130° C. to 230° C., and even more preferably 150° C. to 200° C., from the viewpoint of the color of the water-absorbing resin and the drying efficiency. The drying time in this step is preferably 10 minutes to 2 hours, more preferably 20 minutes to 1.5 hours, and even more preferably 30 minutes to an hour.

Setting the drying conditions so as to fall within the above ranges makes it possible to obtain a water-absorbing resin having a desired centrifuge retention capacity (CRC), a desired water-soluble content (Ext), and a desired color.

Note that the above-described drying temperature is ordinarily defined by the temperature of a heating medium (for example, in a case of hot air drying, the drying temperature is defined by the temperature of hot air). However, for a drying method (e.g., microwave drying) in which the drying temperature cannot be defined by the temperature of a heating medium, the drying temperature is defined by the temperature of a particulate hydrogel. The drying temperature may be kept constant throughout this step, or may be changed as appropriate during this step.

The drying condition(s) other than the drying temperature and the drying time (e.g., a wind speed of hot air) may be set appropriately according to the moisture content and the total mass of the particulate hydrogel to be dried as well as the target resin solid content. In a case where band drying is employed, the various conditions disclosed in, for example, International Publication Nos. WO 2006/100300, WO 2011/025012, WO 2011/025013, and WO 2011/111657 can be applied as appropriate.

[3-5] Pulverizing Step and Classification Step

The pulverizing step is a step of pulverizing the dried polymer obtained in the drying step. The classification step is a step of adjusting the particle size of the pulverized polymer obtained in the pulverizing step to fall within a predetermined range, so as to obtain a water-absorbing resin powder. Herein, the water-absorbing resin in a powder form having not been surface-crosslinked yet is referred to as a "water-absorbing resin powder".

Examples of an apparatus used in the pulverizing step encompass a high-speed rotation pulverizer (such as a roll mill, a hammer mill, a screw mill, or a pin mill), a vibration mill, a knuckle-type pulverizer, and a cylindrical mixer. From the viewpoint of the pulverizing efficiency, it is preferable to use the roll mill. These apparatuses may be used in combination as necessary.

The method of adjusting the particle size used in the classification step is not particularly limited. Examples of the method of adjusting the particle size encompass sieve classification involving use of a JIS-standard sieve (JIS Z 8801-1(2000)) and airflow classification.

Note that the adjustment of the particle size of the water-absorbing resin is not limited to being carried out during the pulverizing step and classification step, but may be carried out during the polymerization step (in particular, in a case where reversed phase suspension polymerization or droplet polymerization is employed) or other steps (for example, a granulation step or fine powder recovery step).

(Physical Properties of Water-Absorbing Resin Powder)

A preferred range of the PSD of the water-absorbing resin powder obtained as a result of the above-described series of steps is identical to the preferred range the PSD of the particulate water-absorbing agent, which is described in [2-8]. In the present invention, the PSD of the water-absorbing resin powder can be regarded as being identical to the particle size of the water-absorbing resin particles having been surface-crosslinked and to the particle size of the particulate water-absorbing agent obtained as a final product. As such, it is preferable to carry out the surface-crosslinking step such that the PSD of the water-absorbing resin powder is maintained. Furthermore, it is more preferable to provide a sizing step after the surface-crosslinking step to adjust the particle size of the particulate water-absorbing agent.

Other preferable physical properties of the water-absorbing resin powder are as follows. The CRC (centrifuge retention capacity) is preferably not less than 27 g/g, more preferably not less than 30 g/g, and even more preferably not less than 33 g/g. In consideration of balance between the CRC and other physical properties, the upper limit of the CRC is preferably 60 g/g or less, more preferably 55 g/g or less, and even more preferably 50 g/g or less. The moisture content is preferably 20 mass % or less, more preferably 10 mass % or less, and even more preferably 5 mass % or less. From the viewpoint of balance between the moisture content and other physical properties, the lower limit of the moisture content is preferably 0 mass %, and more preferably approximately 0.1 mass %.

The water-absorbing resin powder has a specific surface area index of not less than 1.5, preferably not less than 1.6, and more preferably not less than 1.7. The specific surface area index can be calculated in accordance with formula (1), which is described above. There is no particular limitation on the upper limit of the specific surface area index of the water-absorbing resin powder. However, in consideration of the productivity in the production procedure, the upper limit of the specific surface area index of the water-absorbing resin powder is preferably 3 or less, and more preferably 2.5 or less.

Note that the specific surface area index of the water-absorbing resin powder can be controlled in the above-described polymerization step, gel-crushing step, pulverizing step, and classification step.

[3-6] Surface-Crosslinking Step

This step is a step of forming, in a surface of a water-absorbing resin powder having a certain specific surface area index, a portion with a higher crosslinking density. The surface-crosslinking step includes a moistening and mixing step, a heat treatment step, and a cooling step, for example. In this step, a crosslinking reaction caused by the surface-crosslinking agent occurs on the surface of the water-absorbing resin powder, so that a surface-crosslinked water-absorbing resin (hereinafter, referred to as "water-absorbing resin particles") is obtained.

In one aspect of the present invention, a surface-crosslinking agent having an apparent Hansen solubility parameter of 22.5 $MPa^{1/2}$ to 28.5 $MPa^{1/2}$ is used. In another aspect of the present invention, a surface-crosslinking agent that is a $C_{6-8}$ polyhydric alcohol is used.

[3-6-1] Mixing Step

This step is a step of mixing a solution containing the surface-crosslinking agent (hereinafter, referred to as a "surface-crosslinking agent solution") and the water-absorbing resin powder. As a result of this step, a moistened mixture is obtained.

(Surface-Crosslinking Agent and Surface-Crosslinking Agent Solution)

A compound used as the surface-crosslinking agent may be an organic compound that causes a crosslinking reaction with the water-absorbing resin powder. More specific examples of the surface-crosslinking agent encompass a polyhydric alcohol, an epoxy compound, a polyamine compound, a haloepoxy compound, a condensate of a polyamine compound and a haloepoxy compound, an oxazoline compound, an oxazolidinone compound, an alkylene carbonate compound, a polyvalent glycidyl compound, an oxetane compound, a vinyl ether compound, and a cyclic urea compound. One kind of surface-crosslinking agent may be used alone, or two or more kinds may be used in combination.

The amount of the surface-crosslinking agent to be used (if two or more kinds of surface-crosslinking agents are used, the total amount thereof) is preferably 0.01 parts by mass to 10 parts by mass, more preferably 0.01 parts by mass to 5 parts by mass, and more preferably 0.01 parts by mass to 1 part by mass, with respect to 100 parts by mass of the water-absorbing resin powder. Setting the used amount of the surface-crosslinking agent so as to fall within the above range makes it possible to form an optimum cross-linked structure on the surface of the water-absorbing resin powder. Consequently, it is possible to yield a particulate water-absorbing agent having high physical properties.

The solvent in the surface-crosslinking agent solution is preferably water. The amount of water to be used is preferably 0.1 parts by mass to 20 parts by mass, more preferably 0.3 parts by mass to 15 parts by mass, and even more preferably 0.5 parts by mass to 10 parts by mass, with respect to 100 parts by mass of the water-absorbing resin powder. Setting the used amount of water so as to fall within the above range makes it possible to improve the ease of handling of the surface-crosslinking agent solution, thereby enabling uniform mixing of the surface-crosslinking agent solution and the water-absorbing resin powder.

Alternatively, a hydrophilic organic solvent and water may be used in combination, as needed. The amount of the hydrophilic organic solvent to be used is preferably 10 parts by mass or less, more preferably 5 parts by mass or less, and even more preferably 1 part by mass or less, with respect to 100 parts by mass of the water-absorbing resin powder. Specific examples of the hydrophilic organic solvent encompass: lower alcohols (such as methyl alcohol); ketones (such as acetone); ethers (such as dioxane); amides (such as N,N-dimethylformamide); and sulfoxides (such as dimethylsulfoxide).

In addition, the additive described in [3-7] may be added to the surface-crosslinking agent solution or may be added in the surface-crosslinking step. In this case, the amount of the additive to be added is suitably 5 parts by mass or less with respect to 100 parts by mass of the water-absorbing resin powder.

<Apparent Hansen Solubility Parameter>

In one aspect of the present invention, a surface-crosslinking agent having an apparent Hansen solubility parameter of 22.5 $MPa^{1/2}$ to 28.5 $MPa^{1/2}$ is used. The apparent Hansen solubility parameter of the surface-crosslinking agent is preferably 23.0 $MPa^{1/2}$ to 28.0 $MPa^{1/2}$, and more preferably 24.0 $MPa^{1/2}$ to 27.0 $MPa^{1/2}$. By using the surface-crosslinking agent having the apparent Hansen solubility parameter within the above range, it is possible to yield a particulate water-absorbing agent having both a high liquid absorption speed and a low specific re-wet.

Here, the "Hansen solubility parameter" is a kind of a method for predicting solubility of a certain substance in another substance. The Hansen solubility parameters of various substances are described in Wesley L Archer "Industrial solvents handbook," Marcel Dekker, New York, 1996, pp. 35-68, for example. Also, the Hansen solubility parameter can be calculated by commercially-available calculation software, such as HSPiP (version 4.1.05).

Typically, in order to calculate a solubility parameter, it is necessary to obtain a cohesive energy. For the Hansen solubility parameter, the cohesive energy, which influences a solubility constant, is obtained in accordance with formula (8) below with use of three constants.

$$\text{Hansen solubility parameter} = \{(\delta_D)^2 + (\delta_P)^2 + (\delta_H)^2\}^{1/2} \quad (8),$$

where $\delta_D$ is a solubility constant (unit: $MPa^{1/2}$) generated by a non-polar dispersion energy, $\delta_P$ is a solubility constant (unit: $MPa^{1/2}$) generated by a dipole polar energy, and $\delta_H$ is a solubility constant (unit: $MPa^{1/2}$) generated by a hydrogen bond energy.

Herein, the "apparent Hansen solubility parameter" is set under the presupposition that an additive property is established between Hansen solubility parameters of various kinds of surface-crosslinking agents. For example, assume a case where two kinds of surface-crosslinking agents (surface-crosslinking agent A and surface-crosslinking agent B) are contained in a surface-crosslinking agent solution in a mass ratio of a:b. In this case, the apparent Hansen solubility parameters of the two kinds of surface-crosslinking agents are calculated in accordance with the formula below. Apparent Hansen solubility parameter=Hansen solubility parameter of surface-crosslinking agent A×[a/(a+b)]+Hansen solubility parameter of surface-crosslinking agent B×[b/(a+b)].

In a case where only one kind of surface-crosslinking agent is contained in a surface-crosslinking agent solution, the Hansen solubility parameter of the surface-crosslinking agent solution is regarded as the apparent Hansen solubility parameter.

The surface-crosslinking agent is preferably one or more kinds of compounds having a Hansen solubility parameter of 22.5 $MPa^{1/2}$ to 28.5 $MPa^{1/2}$. Examples of such a compound encompass 1,5-pentanediol, 1,2-hexanediol, 1,3-hexanediol, 1,6-hexanediol, 1,8-octanediol, 1,10-decanediol, 2-methyl-1,3-pentanediol, 2-methyl-2,4-pentanediol, 2-methyl-2-propyl-1,3-propanediol, 3-methyl-1,5-pentanediol, diethylene glycol, triethylene glycol, tripropylene glycol, and 4-methyl-1,3-dioxolane-2-one. From the viewpoint of the ease of handling, the compound is preferably one or more kinds selected from 1,2-hexanediol, 1,3-hexanediol, 1,6-hexanediol, 1,8-octanediol, 2-methyl-1,3-pentanediol, 2-methyl-2,4-pentanediol, 2-methyl-2-propyl-1,3-propanediol, 3-methyl-1,5-pentanediol, triethylene glycol, and 4-methyl-1,3-dioxolane-2-one, and more preferably 1,6-hexanediol. Since 2,2-dimethyl-1,3-propanediol (neopentyl glycol) may give a great adverse effect on health, it is recommended that use of 2,2-dimethyl-1,3-propanediol be avoided.

Among the compounds having a Hansen solubility parameter that is within the above range, a polyhydric alcohol or an alkylene carbonate compound is preferably used, and a dihydric alcohol is more preferably used.

Alternatively, the surface-crosslinking agent having a Hansen solubility parameter of 22.5 $MPa^{1/2}$ to 28.5 $MPa^{1/2}$ and a surface-crosslinking agent having a Hansen solubility parameter outside the above range may be used in combination so as to obtain an apparent Hansen solubility parameter within the above range. Further alternatively, surface-crosslinking agents having Hansen solubility parameters each being outside the above range may be used in combination so as to obtain an apparent Hansen solubility parameter within the above range. In the case where the surface-crosslinking agent having a Hansen solubility parameter outside the above range is used, the surface-crosslinking agent is preferably a compound having a Hansen solubility parameter slightly deviated from the above range. Specifically, the surface-crosslinking agent used in such a case is preferably at least one compound selected from 1,3-dioxolane-2-one (ethylene carbonate), 1,2-propylene glycol, 1,3-propanediol, and 1,4-butanediol, and more preferably ethylene carbonate.

<$C_{6-8}$ Polyhydric Alcohol>

In another aspect of the present invention, a $C_{6-8}$ polyhydric alcohol is used as the surface-crosslinking agent. Such a polyhydric alcohol is preferably one or more kinds selected from 1,2-hexanediol, 1,3-hexanediol, 1,6-hexanediol, 1,8-octanediol, 2-methyl-1,3-pentanediol, 2-methyl-2,4-pentanediol, 2-methyl-2-propyl-1,3-propanediol, 3-methyl-1,5-pentanediol, and triethylene glycol. By using such a polyhydric alcohol as the surface-crosslinking agent, it is possible to yield a particulate water-absorbing agent having both a high liquid absorption speed and a low specific re-wet.

The $C_{6-8}$ polyhydric alcohol is preferably a dihydric alcohol. The reason for this is that such a polyhydric alcohol exhibits properties substantially similar to those of a substance having a suitable apparent Hansen solubility parameter described above.

In the present aspect, the $C_{6-8}$ polyhydric alcohol and another kind of surface-crosslinking agent may be used in combination. Examples of the surface-crosslinking agent that can be used in combination with the $C_{6-8}$ polyhydric alcohol encompass the surface-crosslinking agents listed in <Apparent Hansen Solubility Parameter>. In a case where these surface-crosslinking agents are used in combination, a mass ratio between the $C_{6-8}$ polyhydric alcohol and another surface-crosslinking agent is preferably 95:5 to 5:95. Setting the ratio between the surface-crosslinking agents so as to fall within this range enables the surface-crosslinking agents to exhibit their respective crosslinking effects.

(Mixing Method and Mixing Conditions)

Mixing of the water-absorbing resin powder and the surface-crosslinking agent solution is preferably carried out by spraying or dripping, on the water-absorbing resin powder, the surface-crosslinking agent solution prepared in advance. More preferably, the mixing is carried out by spraying, on the water-absorbing resin powder, the surface-crosslinking agent solution prepared in advance. The device used for the mixing preferably has a torque required to uniformly and reliably mix the water-absorbing resin powder and the surface-crosslinking agent solution. From this viewpoint, the mixing device is preferably a high-speed stirring mixer, and more preferably a high-speed stirring continuous mixer.

The number of revolutions of the high-speed stirring mixer is preferably 100 rpm to 10000 rpm, and more preferably 300 rpm to 2000 rpm.

The temperature of the water-absorbing resin powder to be supplied to the mixing device is preferably 25° C. to 80° C., more preferably 25° C. to 70° C., and even more preferably 25° C. to 60° C., from the viewpoints of the miscibility with the surface-crosslinking agent solution and/or the aggregability of the moistened mixture. The mixing time in which the water-absorbing resin powder and the surface-crosslinking agent solution are mixed is preferably 1 second to 60 minutes, more preferably 3 seconds to 30 minutes, and even more preferably 5 seconds to 10 minutes. In this step, it is preferable to remove a waste gas containing fine particles.

[3-6-2] Heat Treatment Step

This step is a step of heating the moistened mixture obtained in the moistening and mixing step, so as to cause a crosslinking reaction on the surface of the water-absorbing resin powder.

(Heat Treatment Method, Heat Treatment Conditions)

The heat treatment method used in this step may be a method in which the moistened mixture in a stationary state is heated or a method in which the moistened mixture in a flowing state is heated, for example. The method in which the moistened mixture in a flowing state is heated is preferable, since this can heat the moistened mixture uniformly and entirely. In order to bring the moistened mixture into a flowing state, the moistened mixture may be stirred or may be caused to flow with use of hot air. Thus, the device to perform the heat treatment is preferably a stirring dryer or a fluidized bed dryer. Specific examples of the stirring dryer encompass a paddle dryer and a multi-fin processor.

Carrying out a heat treatment on the water-absorbing resin powder at a temperature equal to or higher than approximately 180° C. in the heat treatment step makes it easier to yield a particulate water-absorbing agent having both a high absorption speed and a reduced specific re-wet. The heat treatment temperature is preferably 180° C. to 300° C., more preferably 180° C. to 250° C., and even more preferably 180° C. to 220° C. Setting the heat treatment temperature so as to fall within the range makes it possible to improve the performance of the particulate water-absorbing agent. Here, in a case of indirect heating, the heat treatment temperature means a temperature of a heat transfer surface. Meanwhile, in a case of heating with hot air, the heat treatment temperature means a temperature of the hot air. A waste gas discharged from the heat treatment device has a temperature lower than the heat treatment temperature by 1° C. to 100° C., which varies depending on the amount of the waste gas and/or the evaporated moisture.

In the heat treatment step, the abundance of the surface-crosslinking agent decreases as a result of the crosslinking reaction. Thus, the amount of a surface-crosslinking agent left in the particulate water-absorbing agent having undergone the surface-crosslinking step (i.e., a content of a free-state surface-crosslinking agent) is smaller than the amount of the surface-crosslinking agent added in the mixing step. In the particulate water-absorbing agent having been subjected to the heat treatment, a total content of a free-state surface-crosslinking agent is ordinarily 1 mass ppm to 5000 mass ppm, preferably 1 mass ppm to 4500 mass ppm, and even more preferably 1 mass ppm to 4000 mass ppm.

Here, a description is made as to the fact that examining a content of a free-state compound usable as the surface-crosslinking agent enables a determination as to whether or not the heat treatment step is included in the production method and a determination as to whether or not the compound has been used as the surface-crosslinking agent. For example, the polyhydric alcohol can be used not only as the surface-crosslinking agent but also as a mixing aid in the mixing step. However, in a case where the polyhydric alcohol is added as the mixing aid, the particulate water-absorbing agent does not undergo the heat treatment. Therefore, a content of a free-state polyhydric alcohol in the particulate water-absorbing agent exceeds the above-described range. That is, if a content of a free-state compound in the particulate water-absorbing agent is within the above-described range, it is possible to determine that the compound was added as a surface-crosslinking agent and the heat treatment step is included in the production method.

[3-6-3] Cooling Step

This step is an optional step which is carried out as necessary after the heat treatment step. This step is a step of force-cooling a high-temperature water-absorbing resin having been subjected to the heat treatment step to a predetermined temperature, so as to quickly stop the surface-crosslinking reaction.

(Cooling Method and Cooling Conditions)

The cooling method used in the cooling step may be a method in which the water-absorbing resin in a stationary state is cooled or a method in which the water-absorbing resin in a flowing state is cooled, for example. The method in which the water-absorbing resin in a flowing state is cooled is preferable, since this can cool the water-absorbing resin uniformly and entirely. In order to bring the water-absorbing resin into a flowing state, the water-absorbing resin may be stirred or may be caused to flow with use of cool air. Thus, the device to perform the cool treatment is preferably a stirring dryer or a fluidized bed dryer. Specific examples of the stirring dryer encompass a paddle dryer and a multi-fin processor. The device used as the heat treatment device may be used also as the cooling device by replacing the heating medium with a refrigerant.

The cooling temperature is preferably 40° C. to 100° C., more preferably 40° C. to 90° C., and even more preferably 50° C. to 70° C. Setting the cooling temperature so as to fall within this range makes it possible to quickly stop the crosslinking reaction, thereby improving the performance of the particulate water-absorbing agent. Here, in a case of indirect cooling, the cooling temperature means the temperature of a heat transfer surface. Meanwhile, in a case of cooling with cool air, the cooling temperature means the temperature of the cool air.

[3-7] Adding Step

This step is an optional step of adding various compounds in order to improve the performance of the particulate water-absorbing agent and to give various features to the particulate water-absorbing agent.

Specific examples of the compound encompass a polyvalent metal salt, a cationic polymer, a chelating agent, an inorganic reducing agent, an organic reducing agent, an oxidizing agent, an α-hydroxycarboxylic acid compound, a surfactant, a compound having a phosphorus atom, water-insoluble inorganic fine particles, an organic powder (such as metallic soap), a deodorant, an antimicrobial agent, pulp, and thermoplastic fibers.

The added amount of the compound is set according to the purpose of the particulate water-absorbing agent to be obtained, and is preferably 10 mass % or less, more preferably 5 mass % or less, and even more preferably 1 mass % or less. The above-described compound may be added at any timing in the above-described production procedure of the particulate water-absorbing agent.

[3-8] Other Steps

The method in accordance with the embodiment may include not only the above-described steps but also additional steps such as an evaporated monomer recycling step, a granulation step, a sizing step, a fine powder recycling step, and/or an iron removal step, as necessary. Moreover, the method for producing the particulate water-absorbing agent may further include steps such as a transportation step, a storing step, a filling step, a packing step, and/or a reserving step.

Among the additional steps described above, the "sizing step" encompasses a fine powder removal step carried out after the surface-crosslinking step as well as a classification and pulverization step carried out in a case where the water-absorbing resin has aggregated so as to have a size larger than the desired size. Further, the "fine powder recycling step" includes a step of adding fine powder as it is and a step of adding fine powder, in the form of a large hydrogel, to any step of the production process of the water-absorbing resin.

[4] Purpose of Particulate Water-Absorbing Agent

The particulate water-absorbing agent in accordance with the embodiment of the present invention is preferably used for an absorbent body for an absorbent article such as a paper diaper, a sanitary napkin, and an incontinence pad. In particular, the particulate water-absorbing agent is more preferably used as an absorbent body for a high-concentration paper diaper (containing a large amount of particulate water-absorbing agent per paper diaper), which heretofore has problems in odor and coloration from raw materials. In addition, the particulate water-absorbing agent in accordance with the embodiment of the present invention can exert a higher effect in a case where the particulate water-absorbing agent is positioned in an upper layer part of the absorbent body (in a location closer to the user's body).

The absorbent body may include an absorbent material that is not the particulate water-absorbing agent, e.g., pulp fibers. In this case, the content (core concentration) of the particulate water-absorbing agent in the absorbent body is preferably 30 mass % to 100 mass %, more preferably 40 mass % to 100 mass %, even more preferably 50 mass % to 100 mass %, still more preferably 60 mass % to 100 mass %, particularly preferably 65 mass % to 100 mass %, and most preferably 70 mass % to 100 mass %.

Setting the core concentration so as to fall within the above range makes it possible to maintain an absorbent article in a clean, white-colored condition when the absorbent body is provided in an upper layer part of the absorbent article. In addition, such an absorbent body has excellent diffusivity of urine and/or blood, and therefore is expected to improve its absorbency due to effective liquid distribution.

Aspects of the present invention can also be expressed as follows:

The present invention includes the following features:

<1> A method for producing a particulate water-absorbing agent, including the step of surface-crosslinking a water-absorbing resin powder with use of a surface-crosslinking agent, wherein the water-absorbing resin powder has a specific surface area index of not less than 1.5, the specific surface area index being expressed by formula (1) below, and the surface-crosslinking agent has an apparent Hansen solubility parameter of 22.5 MPa$^{1/2}$ to 28.5 MPa$^{1/2}$:

(specific surface area index)=(specific surface area of water-absorbing resin powder)/($10^8 \times D50^2$)  (1), where:
in formula (1), the unit of the specific surface area index is [1/kg], the unit of the specific surface area is [m$^2$/kg], D50 denotes a mass average particle diameter, and the unit of D50 is [m].

<2> The method described in <1>, wherein the surface-crosslinking agent contains one or more kinds of polyhydric alcohols or alkylene carbonate compounds.

<3> A method for producing a particulate water-absorbing agent, including the step of surface-crosslinking a water-absorbing resin powder with use of a surface-crosslinking agent, wherein the water-absorbing resin powder has a specific surface area index of not less than 1.5, the specific surface area index being expressed by formula (1) below, and the surface-crosslinking agent contains a C$_{6-8}$ polyhydric alcohol:

(specific surface area index)=(specific surface area of water-absorbing resin powder)/($10^8 \times D50^2$)  (1), where:
in formula (1), the unit of the specific surface area index is [1/kg], the unit of the specific surface area is [m$^2$/kg], D50 denotes a mass average particle diameter, and the unit of D50 is [m].

<4> The method described in any one of <1> to <3>, wherein the step of surface-crosslinking the water-absorbing resin powder includes carrying out a heat treatment on the water-absorbing resin powder at a temperature of 180° C. to 300° C.

<5> The method described in any one of <1> to <4>, wherein the water-absorbing resin powder has a D50 within a range of 200 μm to 600 μm.

<6> The method described in any one of <1> to <5>, wherein the surface-crosslinking agent contains one or more kinds selected from the group consisting of 1,2-hexanediol, 1,3-hexanediol, 1,6-hexanediol, 1,8-octanediol, 2-methyl-1,3-pentanediol, 2-methyl-2,4-pentanediol, 2-methyl-2-propyl-1,3-propanediol, 3-methyl-1,5-pentanediol, triethylene glycol, and 4-methyl-1,3-dioxolane-2-one.

<7> The method described in any one of <1> to <6>, wherein the water-absorbing resin powder has a specific surface area index of 3 or less, the specific surface area index being expressed by formula (1).

<8> A particulate water-absorbing agent having a specific surface area index of not less than 1.5, the specific surface area index being expressed by formula (1a) below, and the particulate water-absorbing agent having an alcohol absorbency parameter within a range defined by formulae (2) and (3) below:

(specific surface area index)=(specific surface area of particulate water-absorbing agent)/($10^8 \times D50^2$)  (1a);

CRC(35% EtOH)/CRC≥1.2  (2); and

CRC(60% PG)/CRC≥0.40  (3), where:
in formula (1a), the unit of the specific surface area index is [1/kg], the unit of the specific surface area is [m$^2$/kg], D50 denotes a mass average particle diameter, and a unit of D50 is [m];
in formula (2), CRC (35% EtOH) denotes a CRC measured with use of a 35 mass % aqueous ethanol solution; and
in formula (3), CRC (60% PG) denotes a CRC measured with use of a 60 mass % aqueous 1,2-propylene glycol solution.

<9> The particulate water-absorbing agent described in <8>, including a free-state surface-crosslinking agent in a total content of 1 mass ppm to 5000 mass ppm.

<10> The particulate water-absorbing agent described in <9>, wherein the surface-crosslinking agent contains one or more kinds selected from the group consisting of 1,2-hexanediol, 1,3-hexanediol, 1,6-hexanediol, 1,8-octanediol, 2-methyl-1,3-pentanediol, 2-methyl-2,4-pentanediol, 2-methyl-2-propyl-1,3-propanediol, 3-methyl-1,5-pentanediol, triethylene glycol, and 4-methyl-1,3-dioxolane-2-one.

<11> The particulate water-absorbing agent described in any one of <8> to <10>, wherein the particulate water-absorbing agent has an AAP-2.1 kPa value higher than a CRC value, in a case where each of the AAP-2.1 kPa value and the CRC value is expressed in the unit of (g/g).

<12> The particulate water-absorbing agent described in any one of <8> to <11>, wherein the particulate water-absorbing agent has a Vortex of 50 seconds or less.

<13> The particulate water-absorbing agent described in any one of <8> to <12>, wherein the particulate water-absorbing agent has a D50 within a range of 200 μm to 600 μm.

<14> The particulate water-absorbing agent described in any one of <8> to <13>, wherein the particulate water-absorbing agent has a specific surface area index of 3 or less, the specific surface area index being expressed by formula (1).

<15> The particulate water-absorbing agent described in any one of <8> to <14>, wherein the particulate water-absorbing agent has a specific re-wet of 3.7 g or less.

<16> The particulate water-absorbing agent described in any one of <8> to <15>, wherein the particulate water-absorbing agent has a saline flow conductivity (SFC) of not less than $5 \times 10^{-7} \cdot cm^3 \cdot s \cdot g^{-1}$.

<17> The particulate water-absorbing agent described in any one of <8> to <16>, wherein the particulate water-absorbing agent has a specific re-wet of 3.7 g or less, and the particulate water-absorbing agent has a saline flow conductivity (SFC) of not less than $5 \times 10^{-7} \cdot cm^3 \cdot s \cdot g^{-1}$.

The particulate water-absorbing agent in accordance with the aspect of the present invention may be the one described below. The particulate water-absorbing agent may be provided by optionally combining one or more selected from the aspects <1> to <17>.

A particulate water-absorbing agent having a specific surface area index of not less than 2.0, the specific surface area index being expressed by formula (1) below, the particulate water-absorbing agent having a specific re-wet of 3.7 g or less and a saline flow conductivity (SFC) of not less than $5 \times 10^{-7} \cdot cm^3 \cdot s \cdot g^{-1}$, $$\text{(specific surface area index)} = \text{(specific surface area of particulate water-absorbing agent)}/(10^8 \times D50^2) \quad (1a),$$

where:

in formula (1a), the unit of the specific surface area index is [1/kg], the unit of the specific surface area is [m²/kg], D50 denotes a mass average particle diameter, and the unit of D50 is [m] (it should be noted that the unit of D50 in formula (1) is [m], although the technical field to which the present invention pertains often uses [μm] as the unit of D50).

EXAMPLES

The following description will discuss the present invention in more detail with use of Production Examples, Examples, and Comparative Examples. It will be understood that the present invention is not limited to these Production Examples, Examples, and Comparative Examples. The present invention also encompasses examples derived by combining technical means disclosed in the various Examples.

Electric devices used in the Production Examples, Examples, and Comparative Examples (including electric devices used to measure physical properties of the particulate water-absorbing agent) each used a 200-V or 100-V electric power supply, unless otherwise specified. The physical properties of the particulate water-absorbing agent in accordance with the embodiment of the present invention were measured at a room temperature (20° C. to 25° C.) and at a relative humidity of 50% RH±10%, unless otherwise specified. For convenience, a "liter" may occasionally be denoted by "l" or "L", and "% by mass" may occasionally be denoted by "mass %".

[Method of Measuring Physical Properties of Water-Absorbing Resin]

The following description will discuss a method of measuring physical properties of the water-absorbing resin. In a case where something other than the "water-absorbing resin" is a subject to be measured, the wording "water-absorbing resin" in the description of the method for measuring the physical properties can be replaced with the subject. For example, in a case where the subject to be measured is a water-absorbing resin powder, the "water-absorbing resin" is replaced with the "water-absorbing resin powder". For another example, in a case where the subject to be measured is water-absorbing resin particles, the "water-absorbing resin" is replaced with the "water-absorbing resin particles". For further another example, in a case where the subject to be measured is a particulate water-absorbing agent, the "water-absorbing resin" is replaced with the "particulate water-absorbing agent".

(a) Specific Surface Area

The specific surface area of the water-absorbing resin was obtained by analyzing, with use of analysis software, an image captured by X-ray computed tomography (CT).

<Image-Capturing by X-Ray CT>

1.0 g of the water-absorbing resin was put into a resin container (Container No. 1, 2.5 mL, available from Maruemu Corporation), and the resin container was shaken well so that the water-absorbing resin is distributed uniformly in terms of the particle size. Then, the water-absorbing resin was subjected to a measurement with a microfocus X-Ray CT system "inspeXio SMX-100CT" available from Shimadzu Corporation. The measurement was conducted under the following conditions.

Horizontal size (pixel) of image: 512
Vertical size (pixel) of image: 512
X-ray tube voltage (kV): 50
X-ray tube current (μA): 40
Inch size (inch): 4.0
X-ray filter: Without
SDD (distance between focal point of X-ray source and X-ray detector) (mm): 500
SRD (distance between focal point of X-ray source and rotational center of sample to be measured) (mm): 40
Scanning mode 1: CBCT
Scanning mode 2: normal scanning
Scanning angle: full scanning
The number of views: 1200
Average count: 5
Smoothing: YZ
Slice thickness (mm): 0.008
Slice-to-slice distance (mm): 0.010
Scaling factor: 50
BHC data: Without
High-definition mode: With
FOV XY (maximum image-capturing range XY) (mm): 5
FOV Z (maximum image-capturing range Z) (mm): 4
Voxel size (mm/voxel): 0.010

<Calculation of Specific Surface Area>

The data captured by X-ray CT was analyzed in the following procedures with use of analysis software TRI/3D-PRT-LRG available from Ratoc System Engineering Co., Ltd.

1. From the menu, a selection was made as below: Particle measurement>3D particle>Particle separation>Large particle separation. Then, the EV panel, the BC panel, the EVC panel, and the large particle separation panel were displayed.

2. "L-W" was selected in the Binarize tab of the EVC panel, and the L-value was changed to select a measurement target area having a circular shape. "Execute" was pressed to apply this process to all the slice images (as a result, a measurement area having a circular-column shape as a whole was selected). "ROI OK" was pressed in the large particle separation panel.

3. "L-W" was selected in the Binarize tab of the EVC panel, and the L-value was set at 37580 to select only the particles. "Execute" was pressed. Then, "bD" in the BC panel was selected, and "store" was pressed.

4. The ErsSml tab was selected in the Binary tab in the EVC panel. The particle size was set at 10, and "execute" was pressed. As a result of this operation, small noises were removed.

5. The Invert tab was selected in the Binary tab in the EVC panel, and "execute" was pressed. Similarly, the ErsSml tab was selected, and the particle size was set at 10. Then, "execute" was pressed. Similarly, the Labeling tab was selected, the volume and Max were selected, and the fine particle size was set at 100. Then, "execute" was pressed. The Invert tab was selected again, and "execute" was pressed. As a result of this operation, small noises in the particles were removed, and independent voids were filled up. Then, "particle separation target: OK" in the large particle separation panel was pressed. As a result of this operation, information of the particles from which the noises had been removed and in which the independent voids had been filled up was stored in "b1" in the BC panel.

6. In the L Op tab (inter-channel logical operation process) in the EVC panel, "bD" was subtracted from "b1". Subsequently, the ErsSml tab was selected in the Binary tab in the EVC panel, and the particle size was set at 10. Then, "execute" was pressed. As a result of this operation, independent voids were extracted. Then, "b6" was selected in the BC panel, and "store" was pressed.

7. "b1" was selected in the BC panel, and "display" was pressed. The small particle extraction in the large particle separation panel was selected (the large particle extraction was not selected), and the constriction ratio, "Repair Filter Size", and "Repair Mrg Sml Diameter" were each set at 0. Then, "Exec" was pressed. As a result of this operation, separation and color coding on the particles were executed.

8. The Labeling tab was selected in the 3D tab in the EVC panel. The coordinate value (cycle) was selected, and the fine particle size was set at 10. Then, "execute" was pressed. As a result of this operation, color coding on the particles was executed again in the order of the coordinate values.

9. From the menu, a selection was made as below: Particle measurement>Void in 3D particle>Measurement after separation. The measurement after separation panel was displayed. The edge particle removal, the surface area calculation, and the void calculation were selected. The "Binary 5ch" was selected in the calculation ROI designation.

"registration OK" was pressed, and a folder to store the data was selected. Then, "latest registration data execution" was pressed to carry out calculation processing.

10. From the calculation result, a specific surface area was calculated in accordance with the following formula:

$$\text{Specific surface area (m}^2\text{/kg)} = \text{total particle surface area (mm}^2\text{)}/[\{\text{total particle volume (mm}^3\text{)} - \text{total void volume (mm}^3\text{)}\} \times 1.7(\text{g/cm}^3)].$$

(b-1) CRC (Centrifuge Retention Capacity)

The CRC (centrifuge retention capacity) of the water-absorbing resin was measured in accordance with EDANA method (ERT 441.2-02). Specific procedures therefor are as described below.

First, 0.20 g of the water-absorbing resin was weighed out and placed uniformly into a nonwoven fabric bag (60 mm×60 mm). The bag was then heat-sealed at its opening. Thereafter, the bag was immersed in 1000 mL of a 0.9 mass % aqueous sodium chloride solution that has been adjusted to have a temperature of 25±3° C., for 30 minutes. Then, the bag was pulled up and drained with a centrifuge (H-122 available from Kokusan Co. Ltd.) under the condition of 250 G for three minutes. The mass (W1) (unit: g) of the bag having been drained was measured.

The same operation was carried out on a bag containing no water-absorbing resin. The mass (W2) (unit: g) of the bag was measured. The centrifuge retention capacity (CRC) (unit: g/g) of the water-absorbing resin was obtained in accordance with formula (b) below.

$$CRC(g/g) = \{(W1 - W2)/(\text{mass of water-absorbing resin})\} - 1 \quad (b).$$

(b-2) CRC (35% EtOH) and CRC (60% PG)

The CRC (35% EtOH) was measured according to the procedures of the operation in (b-1) in which the 0.9 mass % aqueous sodium chloride solution was replaced with a 35 mass % aqueous ethanol solution. Also, the CRC (60% PG) was measured according to the procedures of the operation in (b-1) in which the 0.9 mass % aqueous sodium chloride solution was replaced with a 60 mass % aqueous 1,2-propylene glycol solution.

(c) AAP (Fluid Retention Capacity Under Pressure)

The AAP (fluid retention capacity under pressure) of the water-absorbing resin was measured in accordance with EDANA method (ERT 442.2-02). Specific procedures therefor are as described below. In the Examples of the present application, the measurement was carried out not only under the load condition (21.0±0.2 g/cm$^2$) specified by ERT 442.2-02 but also under a load condition of 49.0±0.5 g/cm$^2$. The AAP measured under the load condition 21.0±0.2 g/cm$^2$ is denoted by "AAP-2.1 kPa", whereas the AAP measured under the load condition 49.0±0.5 g/cm$^2$ is denoted by "AAP-4.8 kPa".

First, a measurement container constituted by a plastic support cylinder having an inner diameter of 60 mm and a bottom fused with a stainless metal gauze (mesh size 38 μm) was prepared. Next, 0.900 g of the water-absorbing resin was weighed out and put into the measurement container (over the metal gauze) uniformly. Then, a piston and a weight that could uniformly apply a load of 21.0±0.2 g/cm$^2$ to the water-absorbing resin were placed thereon in this order. Thereafter, the mass (W3) (unit: g) of the entire measurement device was measured.

Subsequently, a glass filter (available from Sogo Laboratory Glass Works Co. Ltd., fine pore diameter: 100 μm to 120 μm) of 90 mm in diameter was placed inside a Petri dish of 150 mm in diameter, and a 0.90 mass % aqueous sodium chloride solution was added thereto so as to be filled to the level of the upper surface of the glass filter. Thereafter, one sheet of filter paper (available from ADVANTEC Toyo, JIS P 3801, model No. 2, thickness: 0.26 mm, retained particle diameter: 5 μm) having a diameter of 90 mm was placed on the glass filter so that the surface of the filter paper was entirely wet and an excess liquid was removed.

The entire measurement device was placed on the wet filter paper, so that the 0.90 mass % aqueous sodium chloride solution was allowed to be absorbed into the water-absorbing resin under the load. After an hour, the mass (W4) (unit: g) of the entire measurement device was measured. In accordance with formula (c) below, the AAP (fluid retention capacity under pressure) of the water-absorbing resin (unit: g/g) was obtained.

$$AAP(g/g)=(W4-W3)/\text{mass of water-absorbing resin} \quad (c).$$

Note that the AAP-4.8 kPa was obtained by the same operation as above except that the piston and weight were replaced with a piston and a weight that could apply a load of 49.0±0.5 g/cm².

(d) Vortex (Water Absorption Speed)

The Vortex (water absorption speed) of the water-absorbing resin was measured in the following procedures.

First, 0.02 parts by mass of Food Blue No. 1 (CAS No. 3844-45-9, a food additive) was added to 1000 parts by mass of a 0.9 mass % aqueous sodium chloride solution, so that the solution was colored. Then, the temperature of the solution was adjusted to 30° C. The resultant was used as a test liquid.

Next, 50 mL of the test liquid was measured and taken into a 100-mL beaker. A cylindrical stirring bar of 40 mm in length and 8 mm in diameter was put into the beaker, and stirring was started at 600 rpm. Subsequently, 2.0 g of the water-absorbing resin was put into the test liquid that was being stirred, and a Vortex (water absorption speed) (unit: second) thereof was measured.

A start point and a terminal point of the measurement of the water absorption speed were set in accordance with the description in "Testing method for water absorption rate of super absorbent polymers" defined in JIS K 7224 (1996). Specifically, a point of time when the water-absorbing resin was put into the test liquid was set as the starting point, whereas a point of time when the cylindrical stirring bar was covered with a gel, which was the water-absorbing resin gelatinized as a result of absorption of the test liquid after being introduced into the test liquid, was set as the terminal point. Then, an interval between the starting point and the terminal point was measured as a Vortex (water absorption speed) (unit: second).

(e) SFC (Saline Flow Conductivity)

The SFC (saline flow conductivity) of the water-absorbing resin was measured in accordance with the SFC measurement method described in U.S. Pat. No. 5,669,894. Specific procedures therefor are as described below.

First, 1.50 g of the water-absorbing resin was uniformly put into an SFC measurement container, and was immersed in artificial urine under a load of 2.1 kPa for 60 minutes. Consequently, the water-absorbing resin was turned into a swollen gel. The gel layer height (L0) of the swollen gel was measured. Then, a 0.69 mass % aqueous sodium chloride solution was caused to pass through the swollen gel under a constant hydrostatic pressure (ΔP). During this, the swollen gel layer was kept under the load of 2.1 kPa.

During the operation in which the liquid was caused to pass through the gel, the amount of the liquid passing through the gel layer was recorded by a computer and a scale balance at intervals of 20 seconds for 10 minutes as a function of time.

The flow rate Fs(T) (unit: g/s) of the liquid passing through the swollen gel was obtained by dividing the increase in mass (g) by the increase in time. Assuming that Ts denoted a point of time when a constant hydrostatic pressure and a stable flow rate Fs were obtained, the value of Fs (T=0) (i.e., the first flow rate Fs (T=0) of the liquid passing through the swollen gel) was calculated by using only Ts and the data obtained in 10 minutes. Note that Fs (T=0) was obtained by extrapolating, to T=0, the result of least square approximation of Fs(T) to time.

In accordance with the above-described operation and the size of the measurement device, the SFC (unit: $\times 10^{-7} \cdot cm^3 \cdot s \cdot g^{-1}$) was calculated in accordance with formula (e) below.

$$SFC=(Fs(T=0)\times L0)/(\rho\times A\times \Delta P) \quad (e),$$

where:

in formula (e),

Fs (T=0) denotes the first flow rate (unit: g/s) of the liquid passing through the gel layer;

L0 denotes the layer height (unit: cm) of the gel layer swollen with artificial urine;

ρ denotes the density (unit: g/cm³) of the 0.69 mass % aqueous sodium chloride solution;

A denotes the area (unit: cm²) of the upper surface of the gel layer; and

ΔP denotes the hydrostatic pressure (dyne/cm²) applied to the gel layer.

There may be a case where the liquid passes through the gel layer too fast to attain a hydrostatic pressure of the above value. In such a case, it is possible to obtain an SFC by replacing the value of ΔP with a value calculated on the basis of the height of the liquid surface of the aqueous sodium chloride solution.

Used as the artificial urine was the one prepared by dissolving, in 994.25 g of pure water, 0.25 g of calcium chloride 2-hydrate, 2.0 g of potassium chloride, 0.50 g of magnesium chloride 6-hydrate, 2.0 g of sodium sulfate, 0.85 g of ammonium dihydrogen phosphate, and 0.15 g of diammonium hydrogen phosphate.

(f) Ext (Water-Soluble Content)

The Ext (water-soluble content) in the water-absorbing resin was measured in accordance with EDANA method (ERT 470.2-02). Specific procedures therefor are as described below.

First, 200 mL of a 0.9 mass % aqueous sodium chloride solution was measured and put into a 250-mL plastic container with a lid. A cylindrical stirring bar of 25 mm in length and 8 mm in diameter was put into the plastic container, and stirring was started at 500 rpm. Subsequently, 1.00 g of the water-absorbing resin was put into the aqueous solution that was being stirred, and a resultant was stirred continuously for 16 hours. As a result of the series of operations, a water-soluble content in the water-absorbing resin was extracted.

An extract obtained by the above operations was filtered with one sheet of filter paper (available from ADVANTEC Toyo, JIS P 3801, model No. 2, thickness: 0.26 mm, retained particle diameter: 5 μm). 50.0 g of a filtrate resulting from the filtering was used as a liquid to be measured (hereinafter, referred to as a "measurement liquid").

Next, titration with a 0.1 N aqueous sodium hydroxide solution was carried out on the measurement liquid until the pH of the measurement liquid became 10. Thereafter, titration with 0.1 N hydrochloric acid was carried out on the measurement liquid until the pH of the measurement liquid became 2.7. Note that the amount of the aqueous sodium hydroxide solution added for the titration is denoted by [NaOH] (unit: mL), and the amount of hydrochloric acid added for the titration is denoted by [HCl] (unit: mL). The same operation was carried out on a 0.9 mass % aqueous sodium chloride solution alone, so that a blank titration amount ([bNaOH], [bHCl]) (unit: mL) was obtained.

From the titration amounts obtained in the above operations and the mean molecular weight (Mw) of the raw material monomer of the water-absorbing resin, the Ext (water-soluble content) (unit: mass %) of the water-absorbing resin was obtained in accordance with formula (f-1) below.

$$\text{Ext(mass \%)}=0.1 \times Mw \times 200 \times 100 \times ([\text{HCl}]-[\text{bHCl}])/ 1000/(\text{mass of water-absorbing resin})/50.0 \quad \text{(f-1)}.$$

There may be a case where the mean molecular weight (Mw) of the raw material monomer of the water-absorbing resin is unknown. In such a case, it is possible to calculate the mean molecular weight (Mw) with use of a neutralization rate (unit: mol %), which can be calculated in accordance with formula (f-2) below with use of the titration amount.

$$\text{Neutralization rate(mol \%)}=\{1-([\text{NaOH}]-[\text{bNaOH}])/ ([\text{HCl}]-[\text{bHCl}])\} \times 100 \quad \text{(f-2)}.$$

(g) PSD (Particle Size Distribution, Mass Average Particle Diameter (D50), Logarithmic Standard Deviation (σζ) of Particle Size Distribution)

The PSD (the particle size distribution, the mass average particle diameter (D50), and the logarithmic standard deviation (σζ) of the mass average particle diameter) of the water-absorbing resin was measured in accordance with the measurement method described in Japanese Patent Application Publication, Tokukai, No. 2004-261797. Specific procedures therefor are as described below.

10.0 g of the water-absorbing resin was charged to JIS-standard sieves (The IIDA TESTING SIEVE, inner diameter: 80 mm) (JIS Z 8801-1 (2000)) or sieves corresponding to the JIS-standard sieves, and was subjected to classification with a vibration classifier (IIDA SIEVE SHAKER, Type: ES-65, Ser. No. 0501) for five minutes. The JIS-standard sieves or the sieves corresponding thereto had mesh sizes of 850 μm, 710 μm, 600 μm, 500 μm, 425 μm, 300 μm, 212 μm, 150 μm, and 45 μm.

After the classification, the particle size distribution was obtained from the masses of the water-absorbing resins remaining in the sieves. Note that the wording "the proportion of particles having a particle diameter of less than 150 μm" refers to the proportion (unit: mass %), by mass, of particles that can pass through the JIS-standard sieve having a mesh size of 150 μm, relative to the entire amount of the water-absorbing resin.

In order to obtain the mass average particle diameter (D50), a graph was prepared by plotting, on a logarithmic probability paper, residual percentages R of the respective particle sizes in relation to the particle size distribution obtained in the above-described manner. Then, from the graph, a particle diameter corresponding to R=50 mass % was read as the mass average particle diameter (D50). The mass average particle diameter (D50) refers to a particle diameter corresponding to those of 50 mass % of the entire amount of the water-absorbing resin.

The logarithmic standard deviation (σζ) of the particle size distribution is calculated in accordance with formula (g) below. A smaller value of σζ indicates a narrower particle size distribution.

$$\sigma\zeta=0.5 \times \ln(X2/X1) \quad \text{(g)}.$$

In formula (g), X1 denotes a particle diameter at R=84.1 mass % and X2 denotes a particle diameter at R=15.9 mass %.

(h) Moisture Content

The moisture content of the water-absorbing resin was measured in accordance with EDANA method (ERT 430.2-02).

Specific procedures therefor are as described below. In the measurement in this Example, the amount (4.0 g) of the sample and the drying temperature (105° C.) defined in ERT 430.2-02 were respectively changed to 1.0 g and 180° C.

First, 1.0 g (mass W6, unit: g) of the water-absorbing resin was weighed out and put into an aluminum cup (mass W5, unit: g) having a bottom surface of approximately 5 cm in diameter. Then, the aluminum cup containing the water-absorbing resin was left at rest in a windless dryer at 180° C., so as to be dried for three hours. After drying, the total mass (W7, unit: g) of the water-absorbing resin and the aluminum cup was measured. Then, the moisture content of the water-absorbing resin (unit: mass %) was calculated in accordance with formula (h) below.

$$\text{Moisture content(mass \%)}=\{1-(W7-W5)/W6\} \times 100 \quad \text{(h)}.$$

Note that the value defined by (100−moisture content) was used as a resin solid content (unit: mass %).

(i) Specific Re-Wet

The specific re-wet of the water-absorbing resin was measured with reference to the measurement method disclosed in Japanese Patent Application Publication, Tokukai, No. 2015-066009 (see FIG. 1). Specific procedures therefor are as described below.

First, 1 g of a water-absorbing resin 2 was uniformly dispersed into a laboratory dish 1 of 90 mm in diameter. 30 cc of a 0.90 mass % aqueous sodium chloride solution was poured to the water-absorbing resin 2. A resultant was left at rest for five minutes, so that the water-absorbing resin 2 was swollen. Then, 10 sheets of filter paper 3 each shaped in a circle having a diameter of 55 mm were placed on the water-absorbing resin 2. Then, a circular-cylindrical weight 4 (500 g, bottom surface diameter: 55 mm) was further placed thereon so as to apply a pressure for 10 seconds.

After application of the pressure, the weight 4 was removed and the filter paper 3 was taken out. The weight of the liquid absorbed by the filter paper 3 was obtained (the weight of the filter paper 3 after liquid absorption—the weight of the filter paper 3 before liquid absorption) as a specific re-wet.

(j) Content of Free-State Surface-Crosslinking Agent

A content of a free-state surface-crosslinking agent in the water-absorbing resin was measured in the following procedures.

First, 1.0 g of the water-absorbing resin was weighed out, and was introduced into a 200-mL beaker. Subsequently, 100 mL of a 0.9 mass % aqueous sodium chloride solution was introduced into the beaker. Then, a cylindrical stirring bar of 40 mm in length and 8 mm in diameter was put into the beaker, and stirring was carried out at 600 rpm for 60 minutes. A resulting supernatant solution was taken out, and a content of a free-state surface-crosslinking agent was obtained by a high performance liquid chromatography.

(k) Evaluation on Performance of Model Absorbent Body

A model absorbent body including the particulate water-absorbing agent in accordance with the embodiment of the present invention was prepared according to the following procedures, and performance of the model absorbent body was evaluated.

1.00 g of the particulate water-absorbing agent was uniformly dispersed in a resin tray having a rectangular inner shape of 7.1 cm×8.1 cm and a depth of 3 cm. A top sheet having a size of 7.0 cm×8.0 cm was placed thereon in such a manner as not to cause movement of the particulate water-absorbing agent. Thus, a model absorbent body was obtained. The material of the resin tray is preferably an ABS resin, an acrylic resin, polypropylene, or Teflon (registered trademark), for example (however, the material of the resin tray is not limited to them). Used as the top sheet was the one taken from Mammy Poko Tape Type (product name) L size available from Unicharm Corporation (purchased in July 2014 in Japan, the number on the bottom of the package: 404088043) (this is not limitative).

With use of this model absorbent body, the absorbing time (acquisition) taken from the point of time when introduction of the test liquid was started and the re-wet amount (re-wet) of the absorbed liquid were measured.

A weight lid (394 g) was placed on the model absorbent body. The weight lid had an outer diameter of 7.0 cm×8.0 cm and a center part having an opening (used to introduce the test liquid) of 2.0 cm in diameter. Subsequently, 30 mL of a 0.9 mass % aqueous sodium chloride solution, which was the test liquid, was carefully introduced through the opening. Simultaneously with the introduction of the test liquid, a time measurement with a stopwatch was started. A period of time (s) taken until the test liquid was absorbed to the model absorbent body and a range of the top sheet that was visually observable via the opening was completely exposed was measured. The period of time was obtained as the absorbing time (s).

When five minutes had elapsed after the introduction of the test liquid was started, the weight lid was removed. Then, 15 pieces of kitchen towel (product name: gekikyusyu kicchin taoru 100 (ultra absorbing kitchen towel 100), available from Oji Nepia Co., Ltd., cut pieces of 7.0 cm×8.0 cm) having been weighed in advance were placed on the model absorbent body. On the pieces of kitchen towel, a pressure weight (1181 g) having the same size (i.e., having the bottom surface of 7.0 cm×8.0 cm) was placed, so that a pressure was given thereto for 10 seconds. Thereafter, the weight and the pieces of kitchen towel were removed, and the weight of the pieces of kitchen towel was measured. From a change in the weight of the pieces of kitchen towel, the amount (g) of test liquid absorbed in the pieces of kitchen towel was calculated. The amount of the liquid was obtained as a re-wet amount (g).

Production Example 1

As a production device for producing the particulate water-absorbing agent in accordance with the embodiment of the present invention, there was prepared a continuous production device constituted by devices for carrying out polymerization, gel-crushing, drying, pulverization, classification, surface-crosslinking (mixing, a heat treatment, cooling), and sizing, a transportation device for coupling these devices, and other auxiliary equipment.

First, there was prepared an aqueous monomer solution (1) consisting of 421.7 parts by mass of an acrylic acid, 140.4 parts by mass of a 48 mass % aqueous sodium hydroxide solution, 1.6 parts by mass of polyethylene glycol diacrylate (average n number: 9), 11.3 parts by mass of a 1.0 mass % aqueous trisodium diethylenetriamine pentaacetate solution, and 395.3 parts by mass of deionized water. The aqueous monomer solution (1) was adjusted to have a temperature of 40° C.

Next, the aqueous monomer solution (1) was continuously supplied to the polymerization device with use of a liquid feed pump. During the supply, 211.9 parts by mass of a 48 mass % aqueous sodium hydroxide solution was additionally supplied thereto, and mixing was carried out with a static mixer provided in piping. Thereafter, 17.6 parts by mass of a 4 mass % aqueous sodium persulfate solution was further added as a polymerization initiator to the mixture, and the mixture was mixed with the static mixer provided in the piping. Used as the polymerization device was a planar endless belt polymerization device having two edges provided with barriers.

The aqueous monomer solution (1) to which the polymerization initiator had been added started polymerization after being supplied to the polymerization device. The polymerization took place continuously, so that a cross-linked hydrogel polymer (hereinafter, referred to as a "hydrogel") (1) having a band-shape was obtained. The polymerization time was three minutes.

The hydrogel (1) obtained as a result of the polymerization step was cut into a piece having a suitable size. Then, a certain amount of the hydrogel (1) was supplied per unit time with use of a screw extruder having an extruding outlet provided with a porous plate, so as to carry out gel-crushing to yield a hydrogel (1) in the form of particles (the number of revolutions of the screw: 160 rpm). The gel grinding energy (GGE) required therefor was 22.3 J/g, and the GGE(2) was 14.0 J/g.

Next, the hydrogel (1) in the form of particles obtained as a result of the gel-crushing step was dried with a through-flow belt type continuous dryer (180° C., 30 minutes).

As a result, a dried polymer (1) was obtained. Subsequently, the dried polymer (1) was continuously supplied to a roll mill so as to be pulverized, and was classified with JIS-standard sieves having opening sizes of 850 μm and 150 μm. As a result, a water-absorbing resin powder (1) having a non-uniformly pulverized shape was obtained. The water-absorbing resin powder (1) thus obtained had a mass average particle diameter (D50) of 416 μm, a CRC (centrifuge retention capacity) of 41.3 g/g, a moisture content of 4.1 mass %, and a specific surface area of 28.0 m$^2$/kg. Thus, the water-absorbing resin powder (1) had a specific surface area index of 1.62.

Example 1

There was prepared a surface-crosslinking agent solution (1) consisting of 0.7 parts by mass of 1,6-hexanediol (Hansen solubility parameter: 25.2 MPa$^{1/2}$, the number of carbon atoms: 6), 0.4 parts by mass of ethylene carbonate (Hansen solubility parameter: 28.7 MPa$^{1/2}$), and 3.9 parts by mass of deionized water. The surface-crosslinking agent contained in the surface-crosslinking agent solution (1) had an apparent Hansen solubility parameter of 26.5.

Subsequently, 5.0 parts by mass of the surface-crosslinking agent solution (1) was uniformly mixed in 100 parts by mass of the water-absorbing resin powder (1). Thereafter, the resulting mixture was subjected to a heat treatment at 210° C. for 35 minutes, so that surface-crosslinked water-absorbing resin particles (1) were obtained. Thereafter, the water-absorbing resin particles were allowed to pass through the JIS-standard sieve having an opening size of 850 μm for sizing. As a result, a particulate water-absorbing agent (1) was obtained. Table 1 shows physical properties of the particulate water-absorbing agent (1).

Example 2

There was prepared a surface-crosslinking agent solution (2) consisting of 0.5 parts by mass of 1,6-hexanediol (Hansen solubility parameter: 25.2 MPa$^{1/2}$, the number of carbon atoms: 6), 0.7 parts by mass of 1,2-propylene glycol (Hansen solubility parameter: 29.1 MPa$^{1/2}$, the number of carbon atoms: 3), and 2.9 parts by mass of deionized water. The surface-crosslinking agent contained in the surface-crosslinking agent solution (2) had an apparent Hansen solubility parameter of 27.5.

Subsequently, 4.1 parts by mass of the surface-crosslinking agent solution (2) was uniformly mixed in 100 parts by mass of the water-absorbing resin powder (1). Thereafter, the resulting mixture was subjected to a heat treatment at 210° C. for 35 minutes, so that surface-crosslinked water-absorbing resin particles (2) were obtained. Thereafter, the water-absorbing resin particles were allowed to pass through the JIS-standard sieve having an opening size of 850 μm for sizing. As a result, a particulate water-absorbing agent (2) was obtained. Table 1 shows physical properties of the particulate water-absorbing agent (2).

Example 3

There was prepared a surface-crosslinking agent solution (3) consisting of 0.7 parts by mass 1,8-octanediol (Hansen solubility parameter: 24.6 MPa$^{1/2}$, the number of carbon atoms: 8), 0.7 parts by mass of 1,2-propylene glycol (Hansen solubility parameter: 29.1 MPa$^{1/2}$, the number of carbon atoms: 3), 2.9 parts by mass of deionized water, and 0.7 parts by mass of ethanol. The surface-crosslinking agent contained in the surface-crosslinking agent solution (3) had an apparent Hansen solubility parameter of 26.9.

Subsequently, 5.0 parts by mass of the surface-crosslinking agent solution (3) was uniformly mixed in 100 parts by mass of the water-absorbing resin powder (1). Thereafter, the resulting mixture was subjected to a heat treatment at 210° C. for 40 minutes, so that surface-crosslinked water-absorbing resin particles (3) were obtained. Thereafter, the water-absorbing resin particles were allowed to pass through the JIS-standard sieve having an opening size of 850 μm for sizing. As a result, a particulate water-absorbing agent (3) was obtained. Table 1 shows physical properties of the particulate water-absorbing agent (3).

Example 4

There was prepared a surface-crosslinking agent solution (4) consisting of 0.5 parts by mass of 1,6-hexanediol (Hansen solubility parameter: 25.2 MPa$^{1/2}$; the number of carbon atoms: 6), 0.5 parts by mass of 1,10-decanediol (Hansen solubility parameter: 23.0 MPa$^{1/2}$; the number of carbon atoms: 10), 2.4 parts by mass of deionized water, and 1.6 parts by mass of ethanol. The surface-crosslinking agent contained in the surface-crosslinking agent solution (4) had an apparent Hansen solubility parameter of 24.1.

Subsequently, 5.0 parts by mass of the surface-crosslinking agent solution (4) was uniformly mixed in 100 parts by mass of the water-absorbing resin powder (1). Thereafter, the resulting mixture was subjected to a heat treatment at 210° C. for 60 minutes, so that surface-crosslinked water-absorbing resin particles (4) were obtained. Thereafter, the water-absorbing resin particles were allowed to pass through the JIS-standard sieve having an opening size of 850 μm for sizing. As a result, a particulate water-absorbing agent (4) was obtained. Table 1 shows physical properties of the particulate water-absorbing agent (4).

Example 5

There was prepared a surface-crosslinking agent solution (5) consisting of 1.0 part by mass of 1,6-hexanediol (Hansen solubility parameter: 25.2 MPa$^{1/2}$, the number of carbon atoms: 6) and 3.0 parts by mass of deionized water. The surface-crosslinking agent contained in the surface-crosslinking agent solution (5) had an apparent Hansen solubility parameter of 25.2.

Subsequently, 4.0 parts by mass of the surface-crosslinking agent solution (5) was uniformly mixed in 100 parts by mass of the water-absorbing resin powder (1). Thereafter, the resulting mixture was subjected to a heat treatment at 210° C. for 50 minutes, so that surface-crosslinked water-absorbing resin particles (5) were obtained. Thereafter, the water-absorbing resin particles were allowed to pass through the JIS-standard sieve having an opening size of 850 μm for sizing. As a result, a particulate water-absorbing agent (5) was obtained. Table 1 shows physical properties of the particulate water-absorbing agent (5).

Example 6

There was prepared a surface-crosslinking agent solution (6) consisting of 1.0 part by mass of 1,5-pentanediol (Hansen solubility parameter: 27.6 MPa$^{1/2}$, the number of carbon atoms: 5) and 3.0 parts by mass of deionized water. The surface-crosslinking agent contained in the surface-crosslinking agent solution (6) had an apparent Hansen solubility parameter of 27.6.

Subsequently, 4.0 parts by mass of the surface-crosslinking agent solution (6) was uniformly mixed in 100 parts by mass of the water-absorbing resin powder (1). Thereafter, the resulting mixture was subjected to a heat treatment at 210° C. for 55 minutes, so that surface-crosslinked water-absorbing resin particles (6) were obtained. Thereafter, the water-absorbing resin particles were allowed to pass through the JIS-standard sieve having an opening size of 850 μm for sizing. As a result, a particulate water-absorbing agent (6) was obtained. Table 1 shows physical properties of the particulate water-absorbing agent (6).

Example 7

There was prepared a surface-crosslinking agent solution (7) consisting of 2.0 parts by mass of triethylene glycol (Hansen solubility parameter: 27.5 MPa$^{1/2}$, the number of carbon atoms: 6) and 3.0 parts by mass of deionized water. The surface-crosslinking agent contained in the surface-crosslinking agent solution (7) had an apparent Hansen solubility parameter of 27.5.

Subsequently, 5.0 parts by mass of the surface-crosslinking agent solution (7) was uniformly mixed in 100 parts by mass of the water-absorbing resin powder (1). Thereafter, the resulting mixture was subjected to a heat treatment at 210° C. for 35 minutes, so that surface-crosslinked water-absorbing resin particles (7) were obtained. Thereafter, the water-absorbing resin particles were allowed to pass through the JIS-standard sieve having an opening size of 850 μm for sizing. As a result, a particulate water-absorbing agent (7) was obtained. Table 1 shows physical properties of the particulate water-absorbing agent (7).

Comparative Example 1

There was prepared a comparative surface-crosslinking agent solution (1) consisting of 0.4 parts by mass of ethylene carbonate (Hansen solubility parameter: 28.7 MPa$^{1/2}$), 0.7 parts by mass of 1,2-propylene glycol (Hansen solubility parameter: 29.1 MPa$^{1/2}$, the number of carbon atoms: 3), and 2.9 parts by mass of deionized water. The surface-crosslinking agent contained in the comparative surface-crosslinking agent solution (1) had an apparent Hansen solubility parameter of 29.0.

Subsequently, 4.0 parts by mass of the comparative surface-crosslinking agent solution (1) was uniformly mixed in 100 parts by mass of the water-absorbing resin powder (1). Thereafter, the resulting mixture was subjected to a heat treatment at 210° C. for 30 minutes, so that surface-crosslinked comparative water-absorbing resin particles (1) were obtained. Thereafter, the comparative water-absorbing resin particles were allowed to pass through the JIS-standard sieve having an opening size of 850 µm for sizing. As a result, a comparative particulate water-absorbing agent (1) was obtained. Table 1 shows physical properties of the comparative particulate water-absorbing agent (1).

Comparative Example 2

There was prepared a comparative surface-crosslinking agent solution (2) consisting of 1.1 parts by mass of ethylene carbonate (Hansen solubility parameter: 28.7 MPa$^{1/2}$) and 2.9 parts by mass of deionized water. The surface-crosslinking agent contained in the comparative surface-crosslinking agent solution (2) had an apparent Hansen solubility parameter of 28.7.

Subsequently, 4.0 parts by mass of the comparative surface-crosslinking agent solution (2) was uniformly mixed in 100 parts by mass of the water-absorbing resin powder (1). Thereafter, the resulting mixture was subjected to a heat treatment at 210° C. for 35 minutes, so that surface-crosslinked comparative water-absorbing resin particles (2) were obtained. Thereafter, the comparative water-absorbing resin particles were allowed to pass through the JIS-standard sieve having an opening size of 850 µm for sizing. As a result, a comparative particulate water-absorbing agent (2) was obtained. Table 1 shows physical properties of the comparative particulate water-absorbing agent (2).

Comparative Example 3

There was prepared a comparative surface-crosslinking agent solution (3) consisting of 0.8 parts by mass of glycerin (Hansen solubility parameter: 34.2 MPa$^{1/2}$; the number of carbon atoms: 3) and 3.0 parts by mass of deionized water. The surface-crosslinking agent contained in the comparative surface-crosslinking agent solution (3) had an apparent Hansen solubility parameter of 34.2.

Subsequently, 3.8 parts by mass of the comparative surface-crosslinking agent solution (3) was uniformly mixed in 100 parts by mass of the water-absorbing resin powder (1). Thereafter, the resulting mixture was subjected to a heat treatment at 210° C. for 40 minutes, so that surface-crosslinked comparative water-absorbing resin particles (3) were obtained. Thereafter, the comparative water-absorbing resin particles were allowed to pass through the JIS-standard sieve having an opening size of 850 µm for sizing. As a result, a comparative particulate water-absorbing agent (3) was obtained. Table 1 shows physical properties of the comparative particulate water-absorbing agent (3).

Comparative Example 4

There was prepared a comparative surface-crosslinking agent solution (4) consisting of 1.0 part by mass of 1,3-propanediol (Hansen solubility parameter: 31.7 MPa$^{1/2}$, the number of carbon atoms: 3) and 3.0 parts by mass of deionized water. The surface-crosslinking agent contained in the comparative surface-crosslinking agent solution (4) had an apparent Hansen solubility parameter of 31.7.

Subsequently, 4.0 parts by mass of the comparative surface-crosslinking agent solution (4) was uniformly mixed in 100 parts by mass of the water-absorbing resin powder (1). Thereafter, the resulting mixture was subjected to a heat treatment at 210° C. for 35 minutes, so that surface-crosslinked comparative water-absorbing resin particles (4) were obtained. Thereafter, the comparative water-absorbing resin particles were allowed to pass through the JIS-standard sieve having an opening size of 850 µm for sizing. As a result, a comparative particulate water-absorbing agent (4) was obtained. Table 1 shows physical properties of the comparative particulate water-absorbing agent (4).

Comparative Example 5

There was prepared a comparative surface-crosslinking agent solution (5) consisting of 0.4 parts by mass of 1,4-butanediol (Hansen solubility parameter: 28.9 MPa$^{1/2}$, the number of carbon atoms: 4), 0.7 parts by mass of 1,2-propylene glycol (Hansen solubility parameter: 29.1 MPa$^{1/2}$, the number of carbon atoms: 3), and 2.9 parts by mass of deionized water. The surface-crosslinking agent contained in the comparative surface-crosslinking agent solution (5) had an apparent Hansen solubility parameter of 29.0.

Subsequently, 4.0 parts by mass of the comparative surface-crosslinking agent solution (5) was uniformly mixed in 100 parts by mass of the water-absorbing resin powder (1). Thereafter, the resulting mixture was subjected to a heat treatment at 210° C. for 40 minutes, so that surface-crosslinked comparative water-absorbing resin particles (5) were obtained. Thereafter, the water-absorbing resin particles were allowed to pass through the JIS-standard sieve having an opening size of 850 µm for sizing. As a result, a comparative particulate water-absorbing agent (5) was obtained. Table 1 shows physical properties of the comparative particulate water-absorbing agent (5).

Comparative Example 6

There was prepared a comparative surface-crosslinking agent solution (6) consisting of 0.5 parts by mass of 1,3-propanediol (Hansen solubility parameter: 31.7 MPa$^{1/2}$, the number of carbon atoms: 3), 0.5 parts by mass of 1,2-propylene glycol (Hansen solubility parameter: 29.1 MPa$^{1/2}$, the number of carbon atoms: 3), and 3.0 parts by mass of deionized water. The surface-crosslinking agent contained in the comparative surface-crosslinking agent solution (6) had an apparent Hansen solubility parameter of 30.4.

Subsequently, 4.0 parts by mass of the comparative surface-crosslinking agent solution (6) was uniformly mixed in 100 parts by mass of the water-absorbing resin powder (1). Thereafter, the resulting mixture was subjected to a heat treatment at 210° C. for 40 minutes, so that surface-crosslinked comparative water-absorbing resin particles (6) were obtained. Thereafter, the comparative water-absorbing resin particles were allowed to pass through the JIS-standard sieve having an opening size of 850 µm for sizing. As a result, a comparative particulate water-absorbing agent (6) was obtained. Table 1 shows physical properties of the comparative particulate water-absorbing agent (6).

Comparative Example 7

The same operation as in Example 2 was carried out except that the surface-crosslinking agent solution (2) was replaced with a comparative surface-crosslinking agent solution (7) consisting of 0.05 parts by mass of 1,6-hexanediol (Hansen solubility parameter: 25.2 MPa$^{1/2}$, the number of carbon atoms: 6), 1.0 part by mass of 1,2-propylene glycol (Hansen solubility parameter: 29.1 MPa$^{1/2}$, the number of carbon atoms: 3), and 2.9 parts by mass of deionized water. As a result, comparative water-absorbing resin particles (7) were obtained. The surface-crosslinking agent contained in the surface-crosslinking agent solution (2) had an apparent Hansen solubility parameter of 28.9. Thereafter, the comparative water-absorbing resin particles were allowed to pass through the JIS-standard sieve having an opening size of 850 μm for sizing. As a result, a comparative particulate water-absorbing agent (7) was obtained. Table 1 shows physical properties of the comparative particulate water-absorbing agent (7).

Comparative Example 8

An attempt was made to prepare a surface-crosslinking agent solution (apparent Hansen solubility parameter: 20.6) consisting of 2.0 parts by mass of 1,12-dodecanediol (Hansen solubility parameter: 20.6 MPa$^{1/2}$; the number of carbon atoms: 12) and 6.0 parts by mass of deionized water. However, 1,12-dodecanediol was hardly dissolved, and the target surface-crosslinking agent solution could not be obtained.

Production Example 2

By carrying out the same operation as in Production Example 1 except that the amount of polyethylene glycol diacrylate (average n number: 9) was changed from 1.6 parts by mass to 1.8 parts by mass, a hydrogel (2) and a water-absorbing resin powder (2) were obtained. The gel grinding energy (GGE) required for the gel-crushing step was 24.5 J/g, and the GGE(2) was 15.2 J/g. The resulting water-absorbing resin powder (2) had a mass average particle diameter (D50) of 392 μm, a CRC (centrifuge retention capacity) of 36.2 g/g, a moisture content of 3.9 mass %, and a specific surface area of 26.5 m$^2$/kg. Thus, the water-absorbing resin powder (2) had a specific surface area index of 1.72.

Example 8

By carrying out the same operation as in Example 1 except that the water-absorbing resin powder (1) was replaced with the water-absorbing resin powder (2) and the heat treatment time was changed from 35 minutes to 30 minutes, water-absorbing resin particles (8) were obtained. Thereafter, the water-absorbing resin particles were allowed to pass through the JIS-standard sieve having an opening size of 850 μm for sizing. As a result, a particulate water-absorbing agent (8) was obtained. Table 1 shows physical properties of the particulate water-absorbing agent (8).

Production Example 3

By carrying out the same operation as in Production Example 1 except that the amount of polyethylene glycol diacrylate (average n number: 9) was changed from 1.6 parts by mass to 1.0 part by mass, a hydrogel (3) and a water-absorbing resin powder (3) were obtained. The gel grinding energy (GGE) required for the gel-crushing step was 21.6 J/g, and the GGE(2) was 13.3 J/g. The water-absorbing resin powder (3) thus obtained had a mass average particle diameter (D50) of 396 μm, a CRC (centrifuge retention capacity) of 47.0 g/g, a moisture content of 3.7 mass %, and a specific surface area of 25.5 m$^2$/kg. Thus, the water-absorbing resin powder (3) had a specific surface area index of 1.63.

Example 9

By carrying out the same operation as in Example 1 except that the water-absorbing resin powder (1) was replaced with the water-absorbing resin powder (3) and the heat treatment time was changed from 35 minutes to 40 minutes, water-absorbing resin particles (9) were obtained. Thereafter, the water-absorbing resin particles were allowed to pass through the JIS-standard sieve having an opening size of 850 μm for sizing. As a result, a particulate water-absorbing agent (9) was obtained. Table 1 shows physical properties of the particulate water-absorbing agent (9).

Comparative Production Example 1

By carrying out the same operation as in Production Example 1 except that the number of revolutions of the screw was changed to 110 rpm, a comparative hydrogel (1) and a comparative water-absorbing resin powder (1) were obtained. The gel grinding energy (GGE) required for the gel-crushing step was 17.6 J/g, and the GGE(2) was 8.1 J/g. The comparative water-absorbing resin powder (1) thus obtained had a mass average particle diameter (D50) of 420 μm, a CRC (centrifuge retention capacity) of 40.7 g/g, a moisture content of 3.9 mass %, and a specific surface area of 22.3 m$^2$/kg. Thus, the comparative water-absorbing resin powder (1) had a specific surface area index of 1.26.

Comparative Example 9

By carrying out the same operation as in Example 2 except that the water-absorbing resin powder (1) was replaced with the comparative water-absorbing resin powder (1) and the heat treatment time was changed from 35 minutes to 40 minutes, comparative water-absorbing resin particles (9) were obtained. Thereafter, the comparative water-absorbing resin particles were allowed to pass through the JIS-standard sieve having an opening size of 850 μm for sizing. As a result, a comparative particulate water-absorbing agent (9) was obtained. Table 1 shows physical properties of the comparative particulate water-absorbing agent (9).

Comparative Example 10

By carrying out the same operation as in Comparative Example 1 except that the water-absorbing resin powder (1) was replaced with the comparative water-absorbing resin powder (1) and the heat treatment time was changed from 30 minutes to 40 minutes, comparative water-absorbing resin particles (10) were obtained. Thereafter, the comparative water-absorbing resin particles were allowed to pass through the JIS-standard sieve having an opening size of 850 μm for sizing. As a result, a comparative particulate water-absorbing agent (10) was obtained. Table 1 shows physical properties of the comparative particulate water-absorbing agent (10).

Production Example 4

By carrying out the same operation as in Comparative Production Example 1 except that the amount of deionized water was changed from 395.3 parts by mass to 390.5 parts by mass and 4.8 parts by mass of 1.0 mass % polyoxyethylene (20) sorbitan monostearate (available from Kao corporation) was added, a hydrogel (4) and a water-absorbing resin powder (4) were obtained. The gel grinding energy (GGE) required for the gel-crushing step was 25.0 J/g, and the GGE(2) was 15.8 J/g. The resulting water-absorbing resin powder (4) had a mass average particle diameter (D50) of 375 µm, a CRC (centrifuge retention capacity) of 41.5 g/g, a moisture content of 4.1 mass %, and a specific surface area of 20.6 m²/kg. Thus, the water-absorbing resin powder (4) had a specific surface area index of 1.46. In Production Example 4, the specific surface area index of the water-absorbing resin powder was adjusted by making use of foaming of the surfactant, rather than by adjusting the gel crushing condition.

Example 10

By carrying out the same operation as in Example 1 except that the water-absorbing resin powder (1) was replaced with the water-absorbing resin powder (4), water-absorbing resin particles (10) were obtained. Thereafter, the water-absorbing resin particles were allowed to pass through the JIS-standard sieve having an opening size of 850 µm for sizing. As a result, a particulate water-absorbing agent (10) was obtained. Table 1 shows physical properties of the particulate water-absorbing agent (10).

Example 11

By carrying out the same operation as in Example 2 except that the water-absorbing resin powder (1) was replaced with the water-absorbing resin powder (4), water-absorbing resin particles (11) were obtained. Thereafter, the water-absorbing resin particles were allowed to pass through the JIS-standard sieve having an opening size of 850 µm for sizing. As a result, a particulate water-absorbing agent (11) was obtained. Table 1 shows physical properties of the particulate water-absorbing agent (11).

Example 12

By carrying out the same operation as in Example 4 except that the water-absorbing resin powder (1) was replaced with the water-absorbing resin powder (4), water-absorbing resin particles (12) were obtained. Thereafter, the water-absorbing resin particles were allowed to pass through the JIS-standard sieve having an opening size of 850 µm for sizing. As a result, a particulate water-absorbing agent (12) was obtained. Table 1 shows physical properties of the particulate water-absorbing agent (12).

Production Example 5

By carrying out the same operation as in Comparative Production Example 1 except that 6.0 parts by mass of sodium hydrogen carbonate (available from Wako Pure Chemical Corporation) was added, a hydrogel (5) and a water-absorbing resin powder (5) were obtained. The gel grinding energy (GGE) required for the gel-crushing step was 23.9 J/g, and the GGE(2) was 15.0 J/g. The water-absorbing resin powder (5) thus obtained had a mass average particle diameter (D50) of 390 µm, a CRC (centrifuge retention capacity) of 41.7 g/g, a moisture content of 3.8 mass %, and a specific surface area of 23.2 m²/kg. Thus, the water-absorbing resin powder (5) had a specific surface area index of 1.53. In Production Example 5, the specific surface area index of the water-absorbing resin powder was adjusted by making use of foaming of a carbonic acid gas, rather than by adjusting the gel crushing condition.

Example 13

By carrying out the same operation as in Example 1 except that the water-absorbing resin powder (1) was replaced with the water-absorbing resin powder (5), water-absorbing resin particles (13) were obtained. Thereafter, the water-absorbing resin particles were allowed to pass through the JIS-standard sieve having an opening size of 850 µm for sizing. As a result, a particulate water-absorbing agent (13) was obtained. Table 1 shows physical properties of the particulate water-absorbing agent (13).

Example 14

By carrying out the same operation as in Example 2 except that the water-absorbing resin powder (1) was replaced with the water-absorbing resin powder (5), water-absorbing resin particles (14) were obtained. Thereafter, the water-absorbing resin particles were allowed to pass through the JIS-standard sieve having an opening size of 850 µm for sizing. As a result, a particulate water-absorbing agent (14) was obtained. Table 1 shows physical properties of the particulate water-absorbing agent (14).

Example 15

By carrying out the same operation as in Example 4 except that the water-absorbing resin powder (1) was replaced with the water-absorbing resin powder (5), water-absorbing resin particles (15) were obtained. Thereafter, the water-absorbing resin particles were allowed to pass through the JIS-standard sieve having an opening size of 850 µm for sizing. As a result, a particulate water-absorbing agent (15) was obtained. Table 1 shows physical properties of the particulate water-absorbing agent (15).

Reference Example 1

By carrying out the same operation as in Example 2 except that the heat treatment temperature was changed from 210° C. to 60° C., reference water-absorbing resin particles (1) were obtained. Thereafter, the reference water-absorbing resin particles were allowed to pass through the JIS-standard sieve having an opening size of 850 µm for sizing. As a result, a reference particulate water-absorbing agent (1) was obtained. That is, the production method of Reference Example 1 does not include the heat treatment step.

TABLE 1

| | Physical Properties of Particulate Water-Absorbing Agents | | | | | | |
|---|---|---|---|---|---|---|---|
| | CRC g/g | AAP(2.1) g/g | AAP(4.8) g/g | Vortex s | SFC × 10⁷ · cm³ · s/g | Specific Re-wet g | SSA |
| Ex. 1 | 32.4 | 34.2 | 27.9 | 39 | 19 | 2.8 | 28.0 |
| Ex. 2 | 33.8 | 34.6 | 27.4 | 37 | 5 | 2.9 | 28.0 |

TABLE 1-continued

Physical Properties of Particulate Water-Absorbing Agents

|        |      |      |      |    |    |     |      |
|--------|------|------|------|----|----|-----|------|
| Ex. 3  | 34.0 | 34.7 | 28.1 | 44 | 8  | 3.4 | 28.0 |
| Ex. 4  | 32.3 | 34.7 | 28.4 | 43 | 17 | 2.8 | 28.0 |
| Ex. 5  | 33.3 | 34.4 | 27.0 | 40 | 5  | 1.9 | 28.0 |
| Ex. 6  | 32.3 | 33.8 | 27.6 | 43 | 8  | 3.1 | 28.0 |
| Ex. 7  | 33.7 | 33.8 | 26.8 | 47 | 6  | 3.0 | 28.0 |
| Ex. 8  | 32.5 | 33.4 | 26.9 | 38 | 6  | 3.0 | 26.5 |
| Ex. 9  | 32.0 | 33.5 | 27.1 | 42 | 18 | 2.4 | 25.5 |
| Ex. 10 | 32.6 | 34.0 | 27.6 | 40 | 16 | 2.7 | 20.6 |
| Ex. 11 | 34.2 | 34.6 | 27.5 | 36 | 5  | 2.6 | 20.6 |
| Ex. 12 | 32.8 | 34.5 | 27.9 | 43 | 15 | 2.6 | 20.6 |
| Ex. 13 | 32.8 | 34.2 | 27.7 | 41 | 19 | 2.8 | 23.2 |
| Ex. 14 | 34.2 | 34.7 | 27.7 | 43 | 5  | 2.6 | 23.2 |
| Ex. 15 | 32.9 | 34.7 | 28.2 | 42 | 18 | 2.8 | 23.2 |
| C Ex. 1 | 33.5 | 33.3 | 26.3 | 44 | 2  | 4.4 | 28.0 |
| C Ex. 2 | 33.2 | 32.4 | 26.8 | 46 | 13 | 4.3 | 28.0 |
| C Ex. 3 | 32.7 | 31.7 | 24.7 | 49 | 4  | 4.0 | 28.0 |
| C Ex. 4 | 32.1 | 31.8 | 25.6 | 50 | 10 | 4.1 | 28.0 |
| C Ex. 5 | 33.0 | 32.7 | 25.5 | 48 | 5  | 4.0 | 28.0 |
| C Ex. 6 | 32.0 | 31.9 | 25.5 | 54 | 11 | 4.9 | 28.0 |
| C Ex. 7 | 32.5 | 32.0 | 25.6 | 51 | 9  | 4.1 | 28.0 |
| C Ex. 9 | 33.8 | 32.5 | 25.6 | 83 | 2  | 7.5 | 22.3 |
| C Ex. 10 | 34.1 | 30.8 | 22.5 | 88 | 2  | 7.5 | 22.3 |

|        | SSA Index | Crosslinking Agent | Mixture Ratio Parts by Mass | Solubility Parameter | Apparent Solubility Parameter | No. of C-Atoms in PA | Surface Treatment ° C./min. |
|--------|-----------|--------------------|-----------------------------|----------------------|-------------------------------|----------------------|------------------------------|
| Ex. 1  | 1.6 | HD/EC    | 0.7/0.4  | 25.2/28.7 | 26.5 | 6/—  | 210/35 |
| Ex. 2  | 1.6 | HD/PG    | 0.5/0.7  | 25.2/29.1 | 27.5 | 6/3  | 210/35 |
| Ex. 3  | 1.6 | OD/PG    | 0.7/0.7  | 24.6/29.1 | 26.9 | 8/3  | 210/40 |
| Ex. 4  | 1.6 | HD/DD    | 0.5/0.5  | 25.2/23.0 | 24.1 | 6/10 | 210/60 |
| Ex. 5  | 1.6 | HD       | 1.0      | 25.2      | 25.2 | 6    | 210/50 |
| Ex. 6  | 1.6 | PD       | 1.0      | 27.6      | 27.6 | 5    | 210/55 |
| Ex. 7  | 1.6 | TEG      | 2.0      | 27.5      | 27.5 | 6    | 210/35 |
| Ex. 8  | 1.7 | HD/EC    | 0.7/0.4  | 25.2/28.7 | 26.5 | 6/—  | 210/30 |
| Ex. 9  | 1.6 | HD/EC    | 0.7/0.4  | 25.2/28.7 | 26.5 | 6/—  | 210/40 |
| Ex. 10 | 1.5 | HD/EC    | 0.7/0.4  | 25.2/28.7 | 26.5 | 6/—  | 210/35 |
| Ex. 11 | 1.5 | HD/PG    | 0.5/0.7  | 25.2/29.1 | 27.5 | 6/3  | 210/35 |
| Ex. 12 | 1.5 | HD/DD    | 0.5/0.5  | 25.2/23.0 | 24.1 | 6/10 | 210/60 |
| Ex. 13 | 1.5 | HD/EC    | 0.7/0.4  | 25.2/28.7 | 26.5 | 6/—  | 210/35 |
| Ex. 14 | 1.5 | HD/PG    | 0.5/0.7  | 25.2/29.1 | 27.5 | 6/3  | 210/35 |
| Ex. 15 | 1.5 | HD/DD    | 0.5/0.5  | 25.2/23.0 | 24.1 | 6/10 | 210/60 |
| C Ex. 1 | 1.6 | EC/PG   | 0.4/0.7  | 28.7/29.1 | 29.0 | —/3  | 210/30 |
| C Ex. 2 | 1.6 | EC      | 1.1      | 28.7      | 28.7 |      | 210/35 |
| C Ex. 3 | 1.6 | Gly     | 0.8      | 34.2      | 34.2 | 3    | 210/40 |
| C Ex. 4 | 1.6 | 1,3-PD  | 1.0      | 31.7      | 31.7 | 3    | 210/35 |
| C Ex. 5 | 1.6 | BD/PG   | 0.4/0.7  | 28.9/29.1 | 29.0 | 4/3  | 210/40 |
| C Ex. 6 | 1.6 | 1,3-PD/PG | 0.5/0.5 | 31.7/29.1 | 30.4 | 3/3  | 210/40 |
| C Ex. 7 | 1.6 | HD/PG   | 0.05/1.00 | 25.2/29.1 | 28.9 | 6/3  | 210/35 |
| C Ex. 9 | 1.3 | HD/PG   | 0.5/0.7  | 25.2/29.1 | 27.5 | 6/3  | 210/35 |
| C Ex. 10 | 1.3 | EC/PG  | 0.4/0.7  | 28.7/29.1 | 29.0 | —/3  | 210/40 |

EC: ethylene carbonate,
PG: 1,2-propylene glycol,
BD: 1,4-butanediol,
PD: 1,5-pentanediol,
HD: 1,6-hexanediol,
OD: 1,8-octanediol,
DD: 1,10-decanediol,
TEG: triethylene glycol,
Gly: glycerin,
1,3-PD: 1,3-propanediol
SSA: specific surface area,
SSA Index: specific surface area index,
PA: polyhydric alcohol,
Ex: Example,
C. Ex.: Comparative Example
(These abbreviations are used also in the other tables.)

(These abbreviations are used also in the other tables.)

The results of Comparative Example 8 are not shown, since a surface-crosslinking agent solution could not be obtained in Comparative Example 8.

[Evaluation of Model Absorbent Bodies]

With use of the particulate water-absorbing agents (1) and (2) and the comparative particulate water-absorbing agents (1), (2), and (9), the absorbing time and the re-wet amount of each model absorbent body were measured. A result thereof is shown in Table 2.

TABLE 2

Evaluation of Model Absorbent Bodies

| | Vortex s | SFC × $10^7$ · $cm^3$ · s/g | Specific Re-Wet g | Absorbing Time s | Re-wet Amount g |
|---|---|---|---|---|---|
| Ex. 1 | 39 | 19 | 2.8 | 189 | 2.6 |
| Ex. 2 | 37 | 5 | 2.9 | 185 | 2.5 |
| C. Ex. 1 | 44 | 2 | 4.4 | 222 | 3.6 |
| C. Ex. 2 | 46 | 13 | 4.3 | 209 | 4.1 |
| C. Ex. 9 | 83 | 2 | 7.5 | 415 | * |

*: In Comparative Example 9, a re-wet amount could not be measured, since absorption of the test liquid was not finished within a time limit (five minutes after introduction of the test liquid).

[Measurement of Content of Free-State Surface-Crosslinking Agent]

For each of the particulate water-absorbing agents (1), (2), (5), and (9), the comparative particulate water-absorbing agent (1), and the reference particulate water-absorbing agent (1), a content of a free-state surface-crosslinking agent was measured. A result thereof is shown in Table 3.

TABLE 3

Contents of Free-State Surface-Crosslinking Agents

| Detected Compound | HD ppm | EG* ppm | PG ppm |
|---|---|---|---|
| Ex. 1 | 1253 | 664 | — |
| Ex. 2 | 814 | — | 3424 |
| Ex. 5 | 786 | — | — |
| Ex. 9 | 819 | 341 | — |
| C. Ex. 1 | — | 940 | 4550 |
| Reference Ex. 1 | 4760 | — | 6442 |

*Since a free-state crosslinking agent was extracted in a 0.9% aqueous sodium chloride solution, EC used as a surface-crosslinking agent was hydrolyzed and detected as EG (ethylene glycol).

[Measurement of Alcohol Absorbency Parameter]

For each of the particulate water-absorbing agents (1), (2), (3), (5), and (9) and the comparative particulate water-absorbing agents (1) and (2), a CRC (35% EtOH) and a CRC (60% PG) were measured. A result thereof is shown in Table 4.

TABLE 4

Alcohol Absorbencies of Particulate Water-Absorbing Agents

| | CRC g/g | CRC(35% EtOH) g/g | CRC(60% PG) g/g | CRC(35% EtOH)/ CRC | CRC(60% PG)/ CRC |
|---|---|---|---|---|---|
| Ex. 1 | 32.4 | 40.1 | 13.2 | 1.24 | 0.41 |
| Ex. 2 | 33.8 | 62.3 | 21.6 | 1.84 | 0.64 |
| Ex. 3 | 34.0 | 55.3 | 19.4 | 1.63 | 0.57 |
| Ex. 5 | 33.3 | 61.4 | 22.8 | 1.84 | 0.68 |
| Ex. 9 | 32.0 | 52.3 | 15.2 | 1.63 | 0.48 |
| C. Ex. 1 | 33.5 | 34.8 | 9.9 | 1.04 | 0.30 |
| C. Ex. 2 | 33.2 | 24.9 | 9.5 | 0.75 | 0.29 |

(Results)

In the particulate water-absorbing agents (the particulate water-absorbing agents (1) to (15)) in accordance with the embodiment of the present invention, the specific re-wets were reduced. Of the specific re-wets of the particulate water-absorbing agents (1) to (15), the highest was 3.4 g. The specific re-wets of the particulate water-absorbing agents (1) to (15) were all 3.7 g or less. Meanwhile, of the specific re-wets of the comparative particulate water-absorbing agents (1) to (10), the lowest was 4.0 g. The specific re-wets of the comparative particulate water-absorbing agents (1) to (10) were all higher than 3.7.

According to a comparison between Comparative Examples 1 to 7 and Examples 1 to 9, it is shown that setting an apparent Hansen solubility parameter of the surface-crosslinking agent to fall within a range of 22.5 $MPa^{1/2}$ to 28.5 $MPa^{1/2}$ results in a reduction in specific re-wet. Also, it is shown that adoption of a $C_{6-8}$ polyhydric alcohol as the surface-crosslinking agent results in a reduction in specific re-wet (see Table 1).

The above relations were also observed in the particulate water-absorbing agents having a large specific surface area produced by making use of foaming of the surfactant or carbonic acid gas (see Examples 10 to 15).

The result of the measurement of the alcohol absorbency parameters shows that the particulate water-absorbing agents in accordance with the embodiment of the present invention have a higher alcohol absorbency than those of the particulate water-absorbing agents of the conventional techniques. Specifically, the particulate water-absorbing agents (1), (2), (3), (5), and (9) satisfied both the condition of CRC (35% EtOH)/CRC≥1.2 and the condition of CRC (60% PG)/CRC≥0.40. On the contrary, the comparative particulate water-absorbing agents (1) and (2) did not satisfy both the condition of CRC (35% EtOH)/CRC≥1.2 and the condition of CRC (60% PG)/CRC≥0.40.

Furthermore, the measurement result also shows that the particulate water-absorbing agents (1) to (15) had a favorable absorption speed and a favorable specific re-wet at the same time (see Table 1), in addition to a reduced specific re-wet. That is, it can be said that, among the particulate water-absorbing agents in accordance with the embodiment of the present invention, the particulate water-absorbing agents (1) to (15) give more advantageous effects.

According to a comparison between the results of Comparative Example 9 and Comparative Example 10, it is shown that a water-absorbing resin powder having a specific surface area index of less than 1.5 could not attain an improved specific re-wet, even if a surface-crosslinking agent therein had an apparent Hansen solubility parameter within a certain range (or even if a surface-crosslinking agent therein was a $C_{6-8}$ polyhydric alcohol). That is, it is shown that the production method in accordance with the aspect of the present invention exerts the effect particularly when applied to a case of producing a particulate water-absorbing agent having a high specific surface area index (see Table 1).

It is shown that the model absorbent bodies produced with use of the particulate water-absorbing agents (1) and (2) achieved an improved performance, as compared to the model absorbent bodies produced with use of the comparative particulate water-absorbing agents (1), (2), and (9). Specifically, the model absorbent bodies produced with use of the particulate water-absorbing agents (1) and (2) exhibited a significantly-reduced absorbing time and a significantly-reduced re-wet amount (see Table 2).

In Reference Example 1, the particulate water-absorbing agent was produced by the production method in which the heat treatment after addition of the surface-crosslinking agent solution was carried out at 60° C., i.e., by the production method not including the heat treatment step. As a result, a total content of a free-state surface-crosslinking agent exceeded 5000 mass ppm. This suggests that, in Reference Example 1, 1,6-hexanediol and 1,2-propylene glycol did not sufficiently function as the surface-crosslinking agents due to the absence of the heat treatment (see Table 3).

INDUSTRIAL APPLICABILITY

A particulate water-absorbing agent produced by a production method in accordance with an aspect of the present invention is suitable for a material of an absorbent body for a paper diaper, for example.

The invention claimed is:

1. A particulate water-absorbing agent having a specific surface area index of not less than 1.5, the specific surface area index being expressed by formula (1a) below, the particulate water-absorbing agent having an alcohol absorbency parameter within a range defined by formulae (2) and (3) below:

(specific surface area index)=(specific surface area of particulate water-absorbing agent)/($10^8 \times D50^2$)    (1a);

CRC(35% EtOH)/CRC≥1.2    (2); and

CRC(60% PG)/CRC≥0.40    (3), where:

in formula (1a), the specific surface area index is [1/kg], the specific surface area unit is [$m^2$/kg], D50 denotes the mass average particle diameter, and the D50 unit is [m];

in formula (2), CRC (35% EtOH) denotes a CRC measured with use of a 35 mass % aqueous ethanol solution; and in formula (3), CRC (60% PG) denotes a CRC measured with use of a 60 mass % aqueous 1,2-propylene glycol solution.

2. The particulate water-absorbing agent according to claim 1, comprising:

water-absorbing resin particles having a surface cross-linked by a surface-crosslinking agent; and a free-state surface-crosslinking agent, wherein the total content of the free-state surface-crosslinking agent is 1 mass ppm to 5000 mass ppm.

3. The particulate water-absorbing agent according to claim 2, wherein the surface-crosslinking agent contains one or more kinds selected from the group consisting of 1,2-hexanediol, 1,3-hexanediol, 1,6-hexanediol, 1,8-octanediol, 2-methyl-1,3-pentanediol, 2-methyl-2,4-pentanediol, 2-methyl-2-propyl-1,3-propanediol, 3-methyl-1,5-pentanediol, triethylene glycol, and 4-methyl-1,3-dioxolane-2-one.

4. The particulate water-absorbing agent according to claim 1, wherein the particulate water-absorbing agent has an AAP-2.1 kPa value higher than a CRC value, in a case where each of the AAP-2.1 kPa value unit is (g/g) and the CRC value unit is (g/g).

5. The particulate water-absorbing agent according to claim 1, wherein the particulate water-absorbing agent has a Vortex of 50 seconds or less.

6. The particulate water-absorbing agent according to according to claim 1, wherein the particulate water-absorbing agent has a D50 within a range of 200 μm to 600 μm.

7. The particulate water-absorbing agent according to claim 1, wherein the particulate water-absorbing agent has a specific surface area index of 3 or less, the specific surface area index being expressed by formula (1a).

8. The particulate water-absorbing agent according to claim 1, wherein the particulate water-absorbing agent has a specific re-wet of 3.7 g or less.

9. The particulate water-absorbing agent according to claim 1, wherein the particulate water-absorbing agent has a saline flow conductivity (SFC) of not less than $5 \times 10^{-7} \cdot cm^3 \cdot s \cdot g^{-1}$.

10. The particulate water-absorbing agent according to claim 1, wherein the particulate water-absorbing agent has a specific re-wet of 3.7 g or less, and the particulate water-absorbing agent has a saline flow conductivity (SFC) of not less than $5 \times 10^{-7} \cdot cm^3 \cdot s \cdot g^{-1}$.

* * * * *